United States Patent [19]

Kunitake et al.

[11] Patent Number: 4,469,621
[45] Date of Patent: Sep. 4, 1984

[54] MOLECULAR AGGREGATE HAVING AN ORDERED STRUCTURE

[75] Inventors: Toyoki Kunitake; Yoshio Okahata, both of Fukuoka, Japan

[73] Assignee: Asahi Kasei Kogyo Kabushiki Kaisha, Osaka, Japan

[21] Appl. No.: 276,447

[22] Filed: Jun. 22, 1981

Related U.S. Application Data

[63] Continuation of Ser. No. 34,699, Apr. 30, 1979, abandoned.

[30] Foreign Application Priority Data

Apr. 28, 1978 [JP] Japan ................. 53-49736
Dec. 8, 1978 [JP] Japan ................. 53-151159

[51] Int. Cl.³ .............. B01F 17/12; B01F 17/16; B01F 17/20; B01F 17/32
[52] U.S. Cl. .................. 252/353; 210/643; 252/312; 252/351; 252/356; 252/357; 252/DIG. 1; 252/DIG. 7; 264/4.1; 428/402.2; 502/4
[58] Field of Search ............. 252/299.2, 299.3, 299.4, 252/357, 351, 353, 356

[56] References Cited

U.S. PATENT DOCUMENTS

| | | | |
|---|---|---|---|
| 3,720,623 | 3/1973 | Cartmell et al. | 252/316 |
| 3,803,050 | 4/1974 | Haas et al. | 252/299.4 X |
| 3,956,169 | 5/1976 | Nakano et al. | 252/299.2 |
| 4,243,549 | 1/1981 | Messenger et al. | 252/357 X |

OTHER PUBLICATIONS

Davies et al.: "Interfacial Phenomena", Second Edition, 1963, Academic Press, New York and London, pp. 370–375.

Schönfeldt: "Surface Active Ethylene Oxide Adducts", Pergamon Press, Printed in Hungary, 1969, pp. 186–194.

*Primary Examiner*—Richard D. Lovering
*Attorney, Agent, or Firm*—Sughrue, Mion, Zinn, Macpeak, and Seas

[57] ABSTRACT

A stable molecular aggregate having an ordered structure comprising a surfactant containing a hydrophilic moiety and hydrophobic moiety and having in the hydrophobic moiety or between the hydrophobic moiety and the hydrophilic moiety a rigid moiety at least 10 Å long is disclosed. The structure, unlike the spherical micelle formed by an ordinary surfactant in water or the loose lamellar micelle formed by a soap in a high concentration, is stable and durable in low concentrations, keeping a high degree of regularity. The structure has primarily a bilayer structure as a basic structural unit.

35 Claims, 25 Drawing Figures

×150,000 (Example 1)

×250,000 (Example 2)

x 200,000 (Example 3)

x 150,000 (Example 4)

x 150,000 (Example 5)

x 200,000 (Example 6)

x 300,000 (Example 7)

x 200,000 (Example 8)

x 300,000 (Example 9)

x 300,000 (Example 10)

x 100,000 (Example 11)

x 300,000 (Example 12)

x 250,000 (Example 13)

x 300,000 (Example 14)

× 300,000 (Example 16)

× 300,000 (Example 17)

×300,000 (Example 18)

×300,000 (Example 19)

× 300,000 (Example 20)

× 300,000 (Example 21)

× 300,000 (Example 22)

× 300,000 (Example 23)

x 300,000 (Example 24)

x 300,000 (Example 25)

MOLECULAR AGGREGATE HAVING AN ORDERED STRUCTURE

This is a continuation of application Ser. No. 34,699, filed Apr. 30, 1979, now abandoned.

BACKGROUND OF THE INVENTION

1. Field of the Invention

This invention relates to a stable molecular aggregate having an ordered structure comprising a surfactant containing a hydrophilic moiety and hydrophobic moiety. More particularly, this invention relates to a molecular aggregate having an ordered structure in which the surfactant contains a rigid moiety.

2. Description of the Prior Art

It is well known that surfactants generally form spherical or loose lamellar micelles in water. It is also well known that phospholipids form a stable bilayer membrane in a biomembrane. Conventional micelles and bilayer membranes are formed of a compound having two long chain hydrophobic groups, and there has been no teaching to date in which a stable bilayer or multilayer structure is formed from a compound having a single long chain hydrophobic group.

SUMMARY OF THE INVENTION

It is, therefore, one object of this invention to provide a stable molecular aggregate having an ordered structure from a compound having a single long chain hydrophobic group, said structure primarily consisting of a bilayer structure as its principal structural unit.

It is another object of the present invention to provide a novel surfactant comprising a hydrophobic moiety and a hydrophilic moiety containing in the hydrophobic moiety or between the hydrophobic moiety and the hydrophilic moiety, a rigid moiety at least 10 Å long.

It is still another object of the present invention to provide a stable molecular aggregate having an ordered structure which can be used effectively in selective permeation, retention, as well as in acceleration or deceleration of a chemical reaction.

It is a further object of the present invention to provide a surfactant capable of forming a stable molecular aggregate having an ordered structure at concentrations lower than the critical concentration of conventional surfactants.

DETAILED DESCRIPTION OF THE INVENTION

Figure 1:
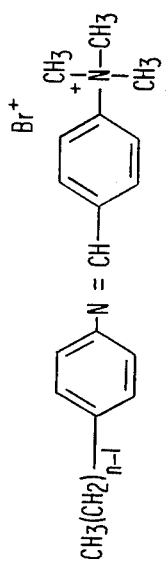
FIG. 1 shows the NMR absorption spectra of the surfactants prepared in Examples 1 and 2 and in Reference Example 1.
Figure 1:
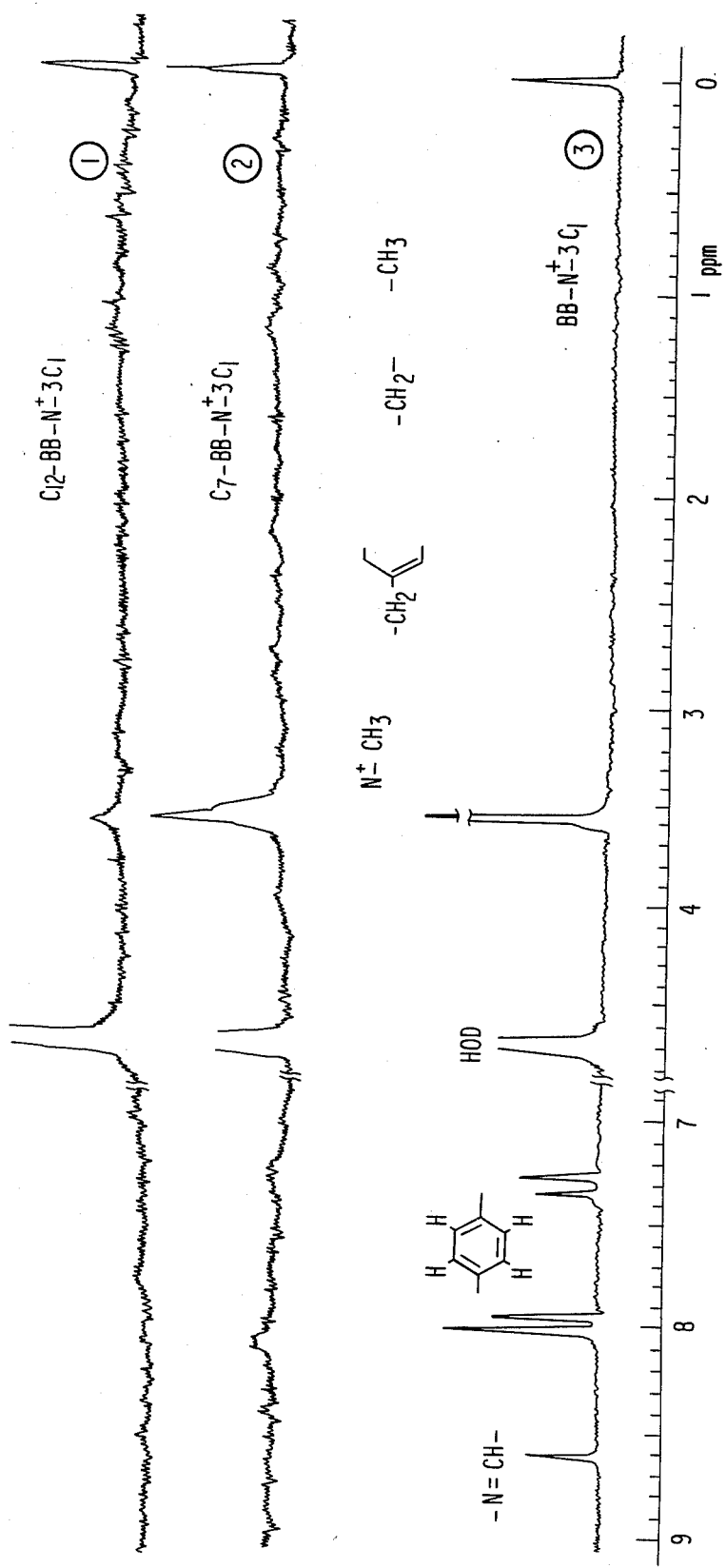
Figure 2:
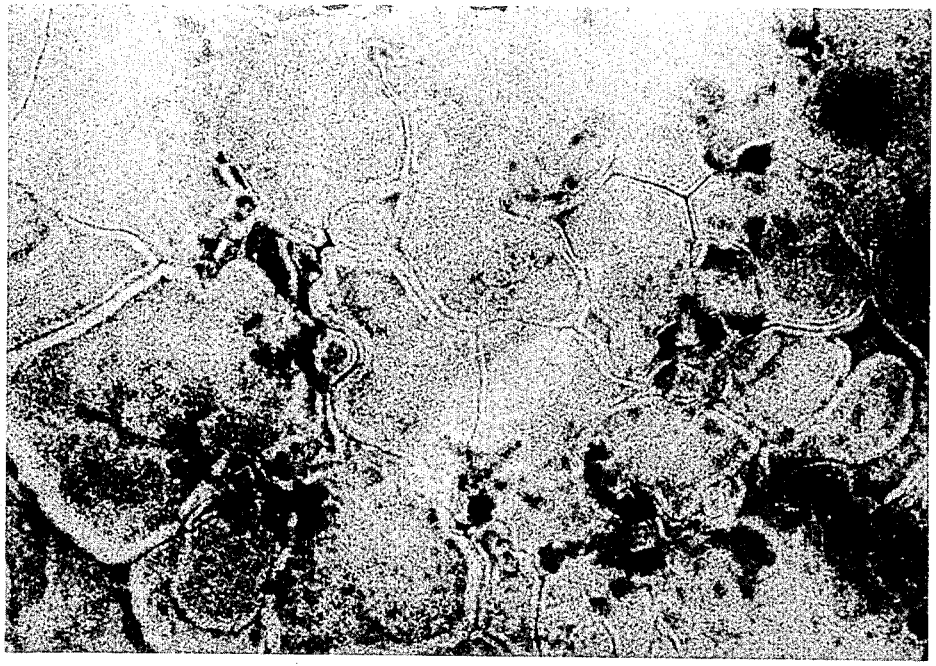
FIGS. 2 to 25 are electron micrographs of the surfactants prepared in Examples 1 to 14 and 16 to 25.
Figure 3:
Figure 4:
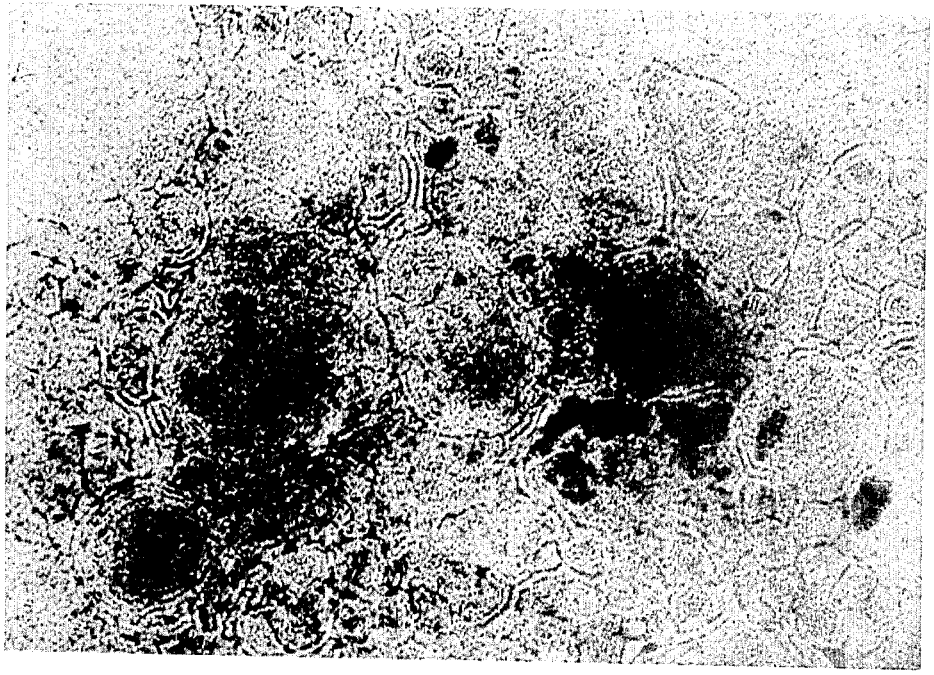
Figure 5:
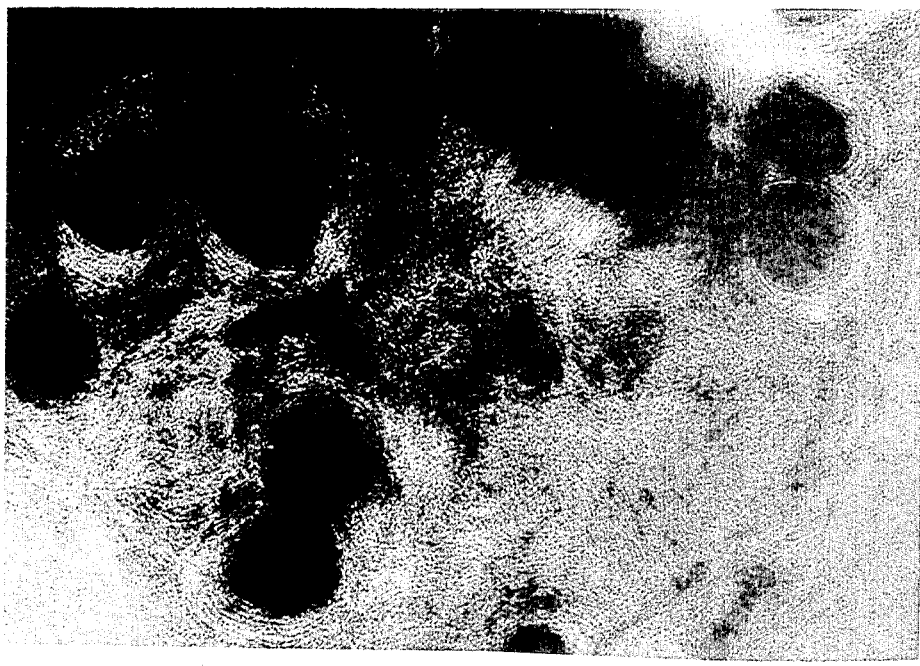
Figure 6:
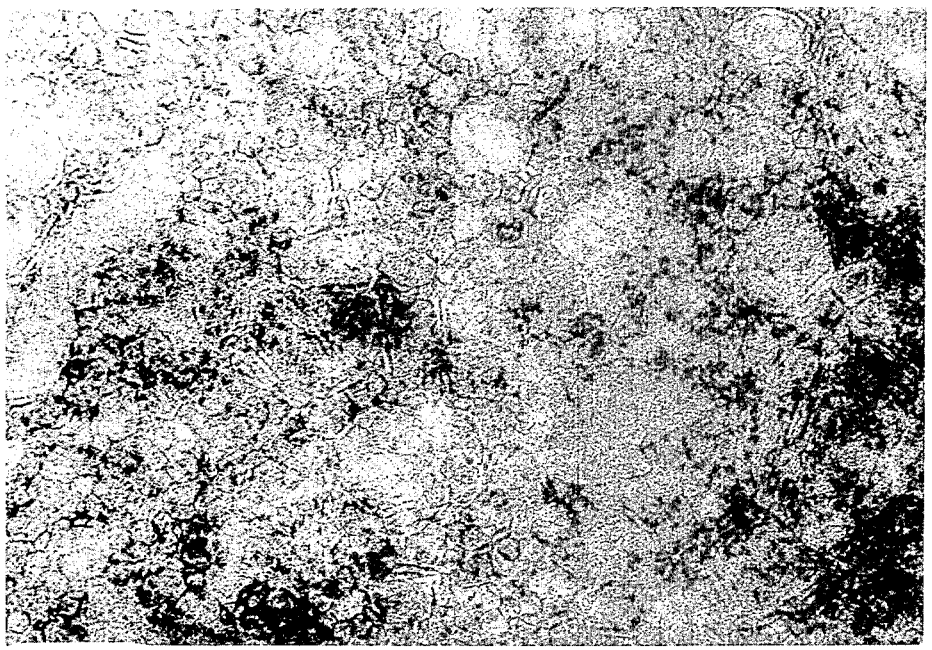
Figure 7:
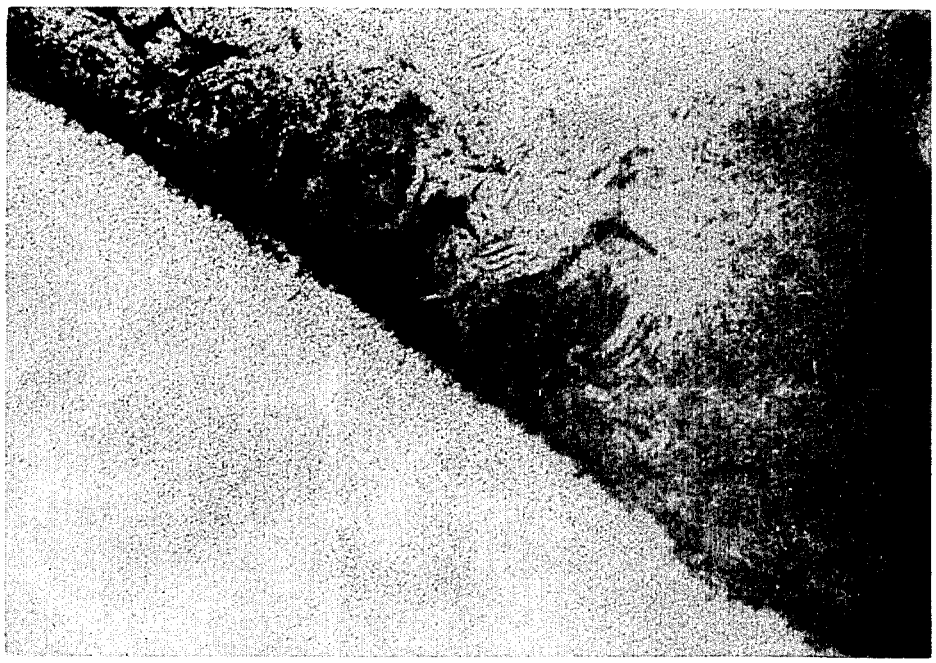
Figure 8:
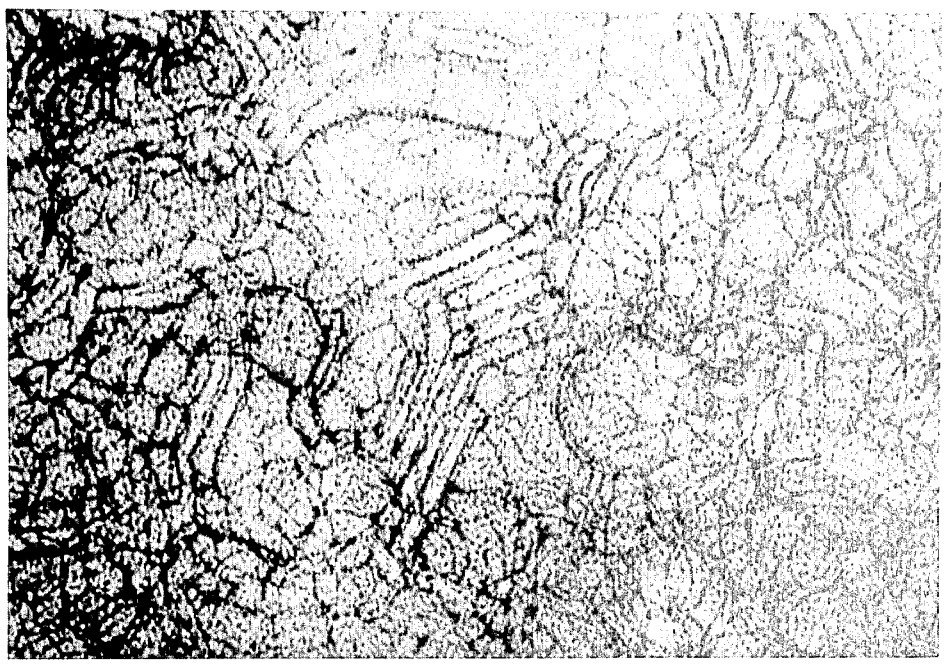
Figure 9:
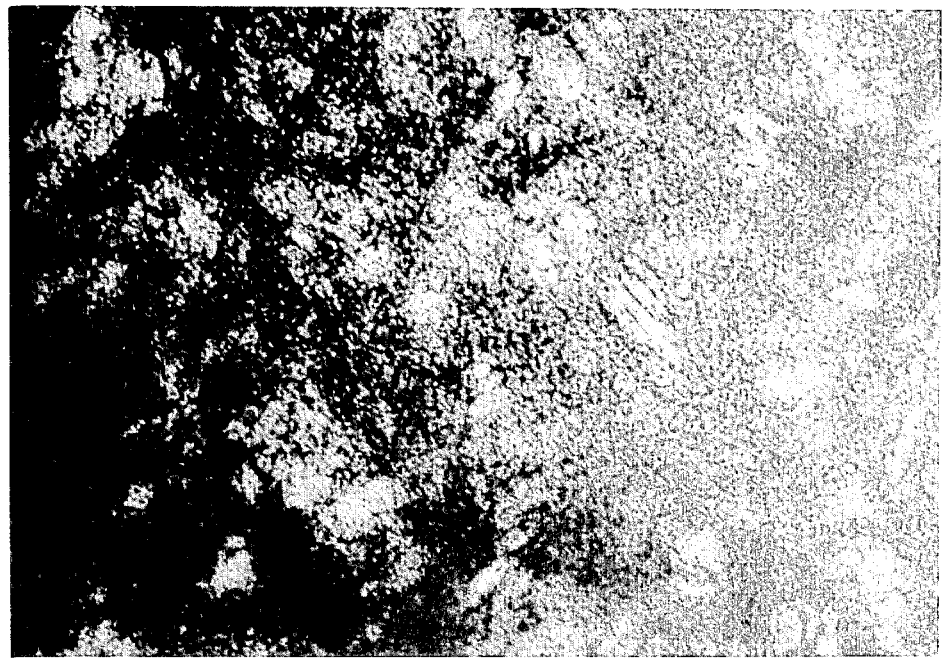
Figure 10:
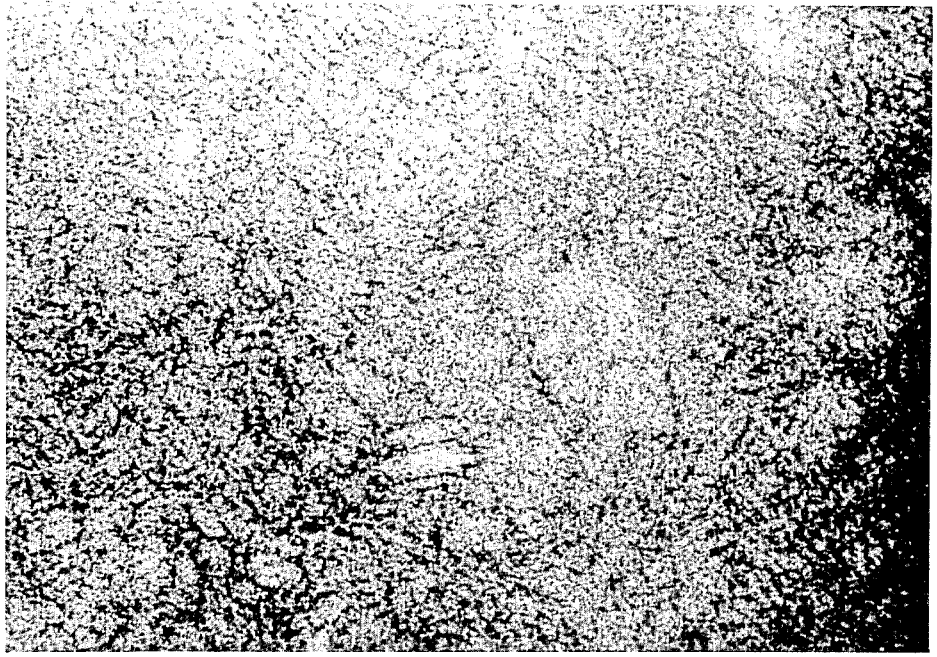
Figure 11:
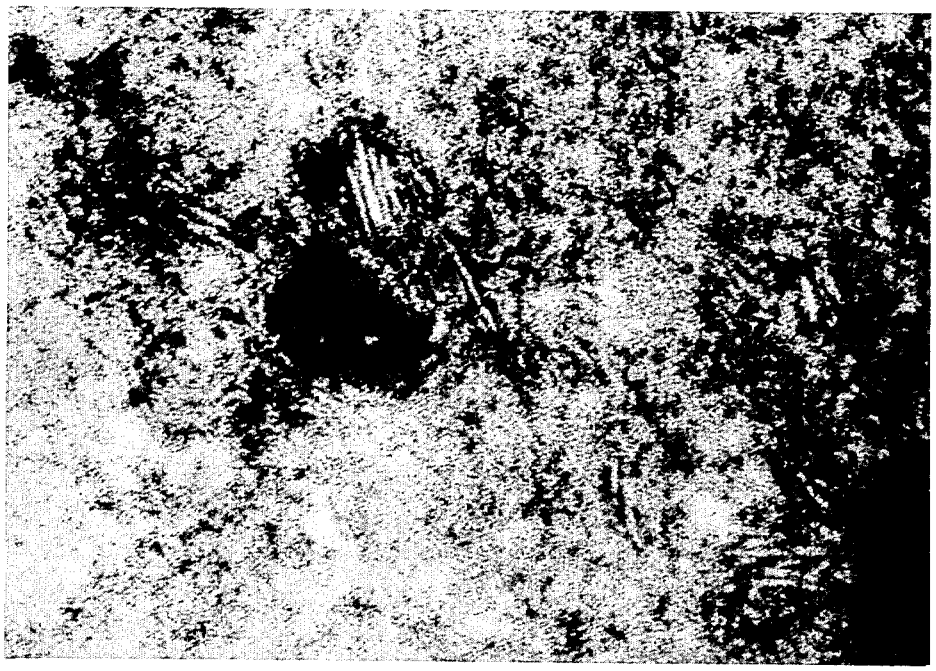
Figure 12:
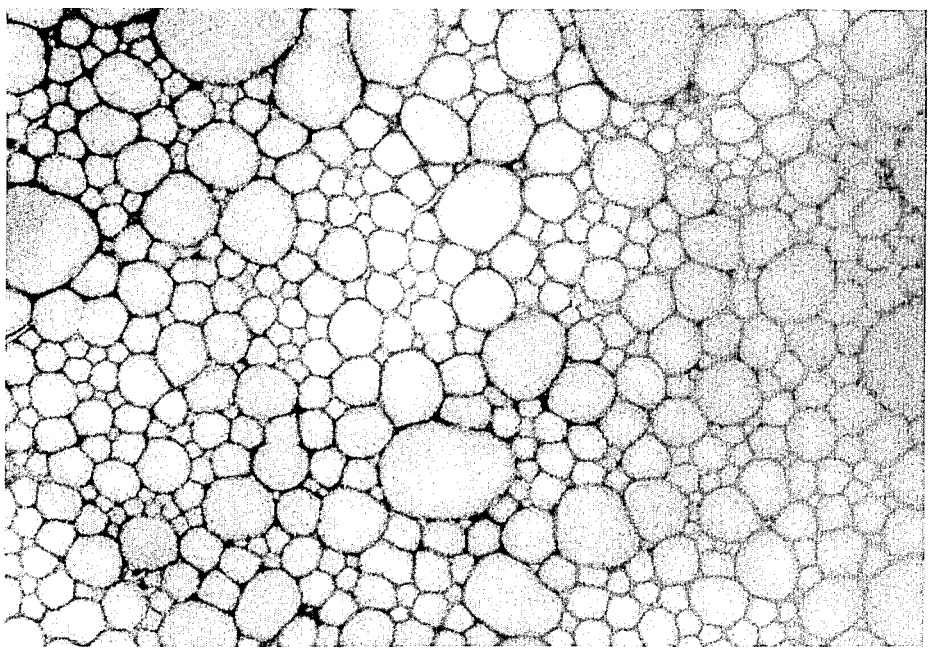
Figure 13:
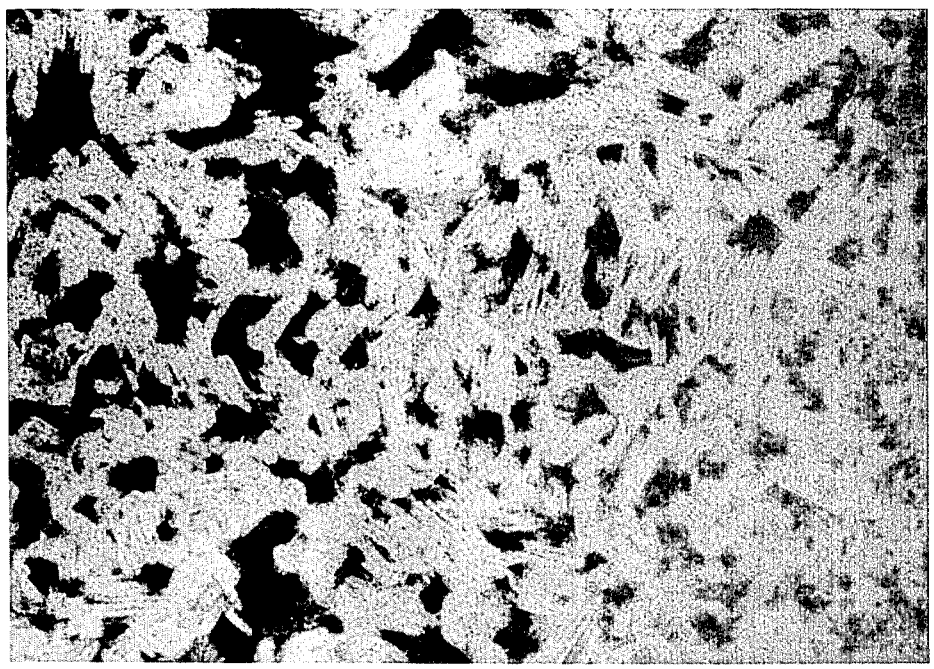

This invention is based on the finding that a surfactant comprising a hydrophilic moiety and hydrophobic moiety and having in the hydrophobic chain a rigid moiety which is at least 10 Å long forms a stable molecular aggregate having an ordered structure which primarily consists of a bilayer structure as its basic structural unit.

The surfactant capable of forming the molecular aggregate having an ordered structure of this invention is represented by the formula (I):

$$Cn-Ya-\phi-Yb-Cm-X \qquad (I)$$

wherein X represents a hydrophilic moiety; $Cn-Ya-\phi-Yb-Cm-$ represents a hydrophobic moiety, containing a rigid moiety $Ya-\phi-Yb$ which is at least 10 Å long.

By the term "rigid moiety" as used herein is meant that moiety of the formula (I) which is expressed by $Ya-\phi-Yb$, wherein $\phi$ is rigid and capable of bounding Ya and Yb linearly or non-linearly.

The rigid moiety $Ya-\phi-Yb$ consists of Ya and Yb which represent divalent coupling groups and $\phi$ which is generally: (1) two to four aromatic rings condensed or bonded directly or through a carbon-carbon multiple bond, a carbon-nitrogen multiple bond, a nitrogen-nitrogen multiple bond, an ester linkage, or an amide bond; (2) at least two aromatic rings coupled by a plurality (2 to 3) of single bonds; (3) a three-dimensionally stablized alicyclic condensed ring, e.g., a compound containing two to four aromatic rings bonded to each other at at least two or more atoms of each ring such as a steroid ring, a saturated condensed ring and a spiro ring; (4) a single bonded chain or a bonded chain consisting of a single bond and multiple bond, which is capable of retaining zigzaging or linearity due to its steric hindrance or energy hindrance. Among examples of the above illustrated $\phi$ are:

Group (1)

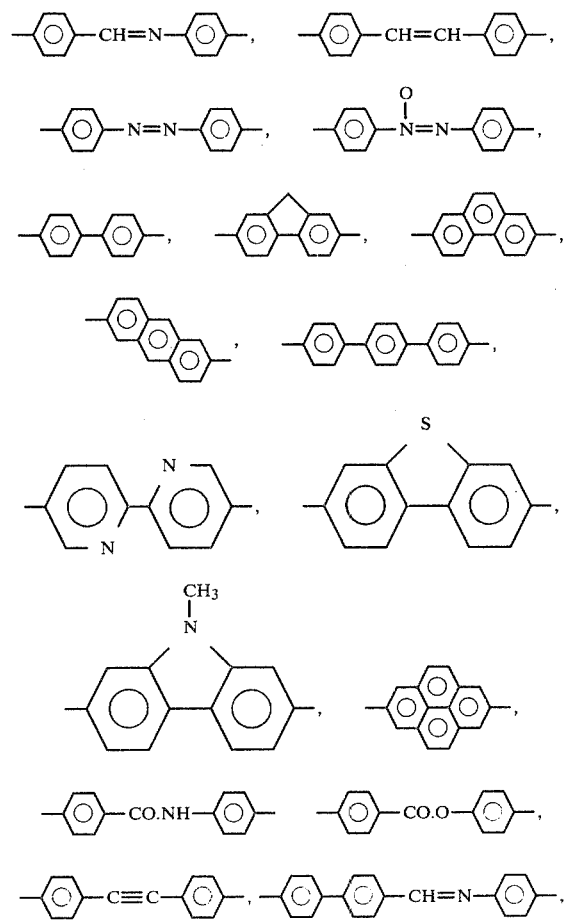

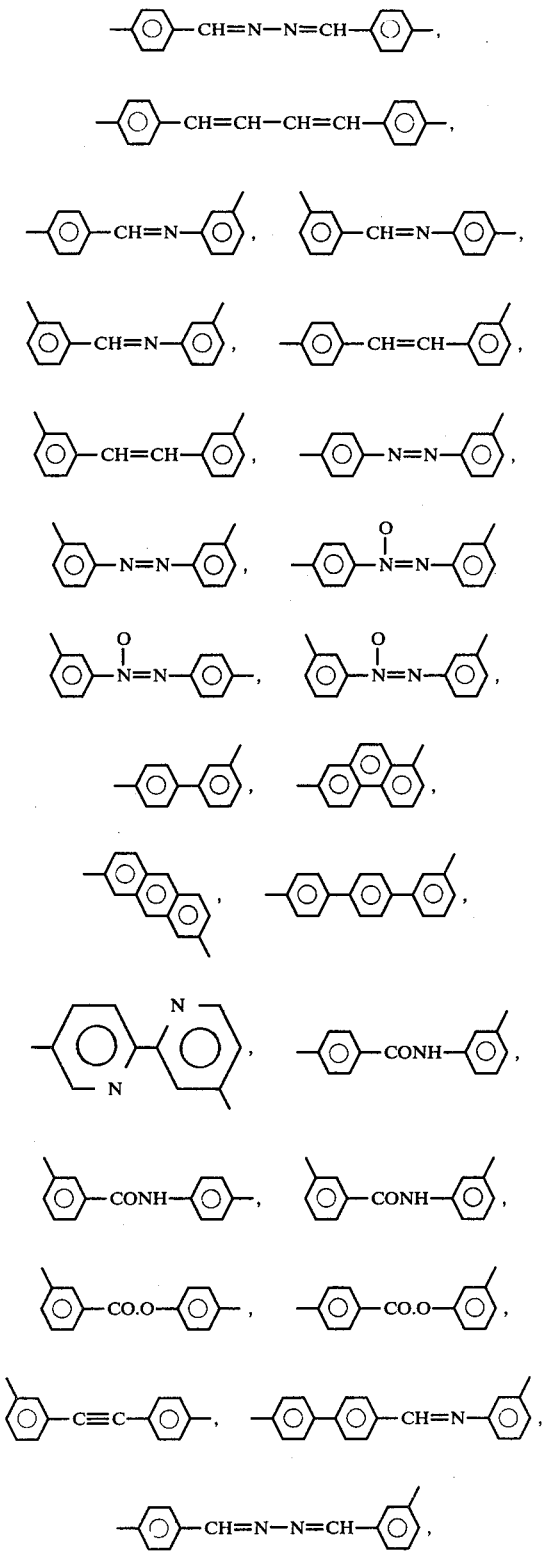
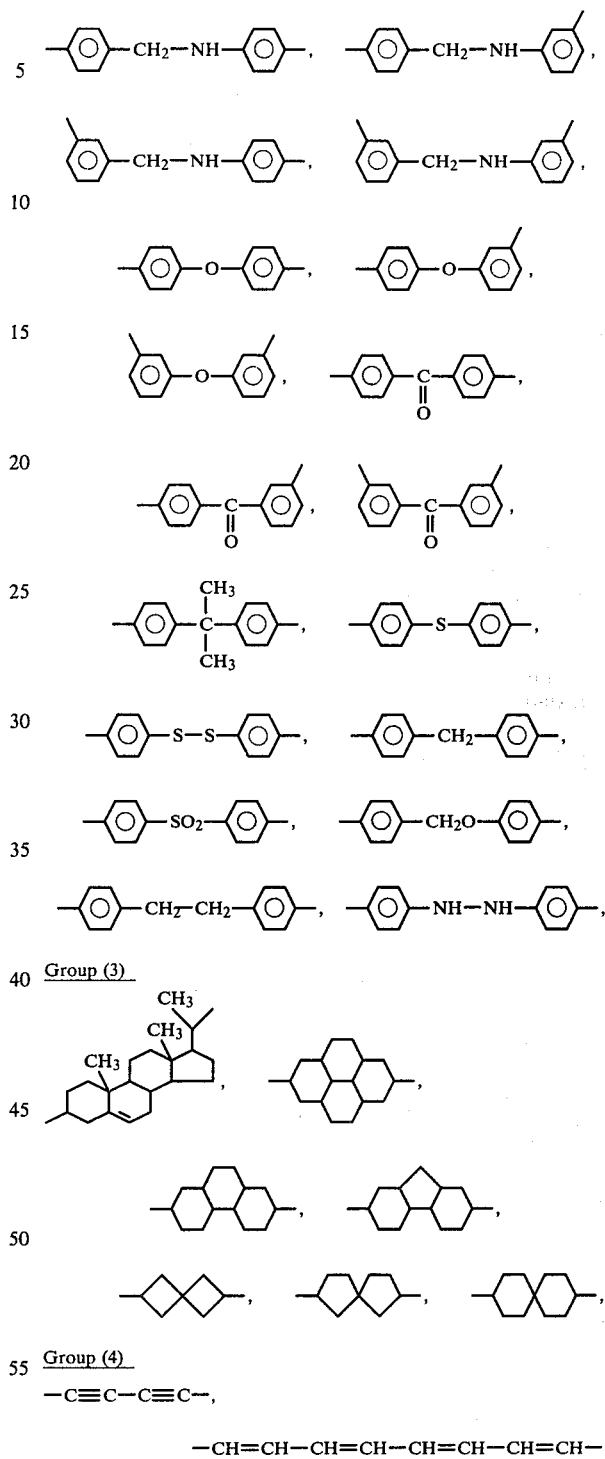
Group (4)
—C≡C—C≡C—,
—CH=CH—CH=CH—CH=CH—CH=CH—
The surfactants of the present invention can easily be synthesized by those skilled in the art using well known synthetic techniques. The —φ— structure as described above can be formed employing known methods.
One of the methods is to react the following reactants —20° to 150° C. to easily form the following —φ— structure.
Group (2)

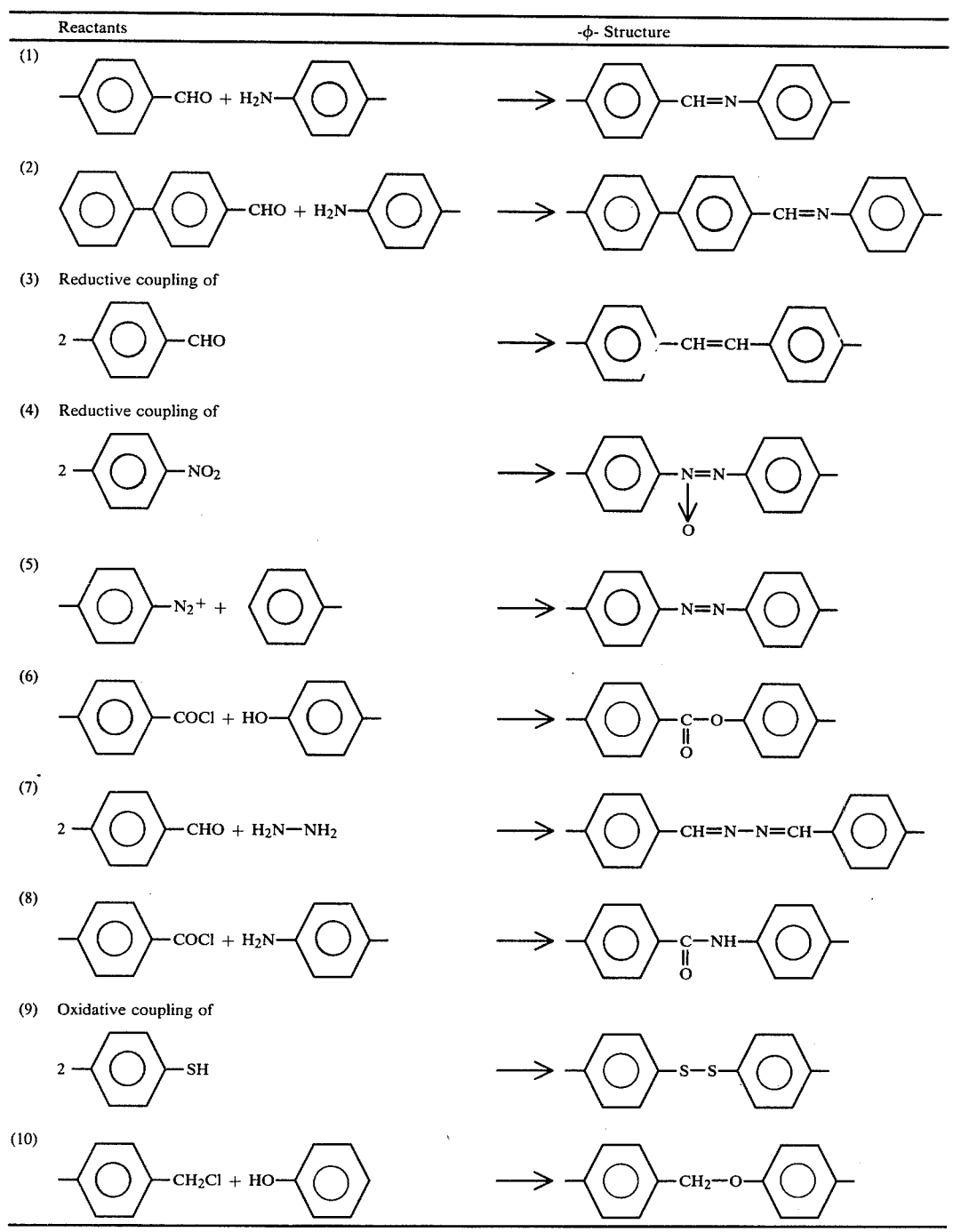
By reducing (e.g., catalytic hydrogenation) the thus-obtained compound above, the following —φ— structure can be formed.
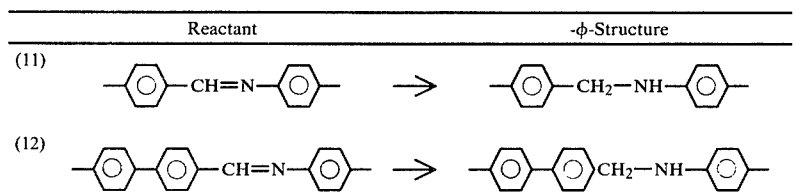

| | -continued | |
|---|---|---|
| | Reactant | -φ-Structure |
| (13) | | 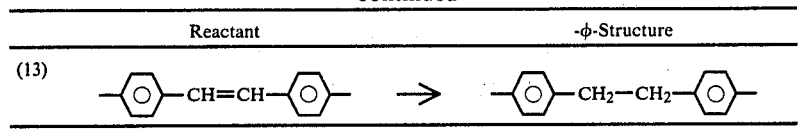 |

On the other hand, when a starting material having the —φ— structure in its molecule is available, it is convenient to perform an alkylation reaction of the corresponding dihydroxy compound

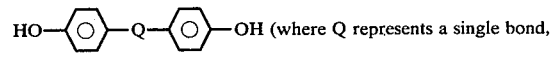 (where Q represents a single bond,

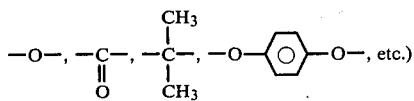 etc.)

in the presence of an alkali. Thus, compounds having the following —φ— structures can be obtained, i.e.,

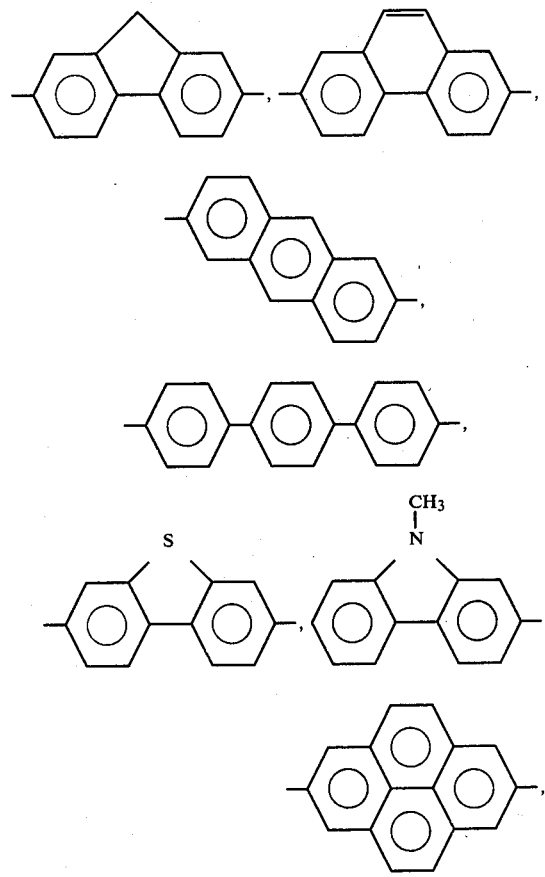

In the same manner as described above, a long chain alkyl group or a hydrophilic group can be introduced for Q' of the cholesterol derivative The surfactants having such a rigid moiety may be used alone or as a mixture to form the aggregate of this invention. Of these, the surfactants having the rigid moiety defined by Groups (1) or (2) are preferred.

Use of a surfactant having a rigid moiety containing a bifunctional residue φ which provides generally linear or parallel relation between bonding axes Ya—φ and Yb—φ in the formula (I) is preferred since it results in improved orderliness of the aggregate, which effects the performance of the aggregate in terms of its selective permeation or retention of a substance (e.g., a microcapsules) as well as in terms of acceleration or deceleration of a chemical reaction (e.g., a catalyst), with good results obtained depending on the application where it is used.

The term "generally lineary or parallel relation between bonding axes Ya—φ and Yb—φ" means that both axes lie on a straight line or they are parallel to each other. For the purpose of this desription it is assumed that the bonding axes Ya—φ and Yb—φ can be considered parallel or linear is estimates based on molecular models or potential energies (in lieu of an actual measurement which is extremely difficult to make) indicate that the two axes form an angle of 20° or less. Examples of the rigid moiety providing such generally linear or parallel bonding axes include the first nineteen examples of the rigid moieties in Group (1) above.

Of these rigid moieties described above, the rigid moiety of (1) at least two benzene rings condensed or bonded directly to one another or through a carbon-carbon multiple bond, a carbon-nitrogen multiple bond, a nitrogen-nitrogen multiple bond, an ester linkage or an amide linkage or (2) at least two benzene rings coupled by two or three of single bonds, having bonded Ya and Yb at 4 position of the benzene rings are particularly preferred since the surfactant having the rigid moiety can form a stable aggregate.

Ya and Yb of the formula (I) are each a divalent coupling group through which φ is bonded to the hydrophobic or hydrophilic moiety, and generally represent —$CH_2$—, —CO—, —O—, NH—, —S—, —$SO_2$—, etc., although φ may be directly bonded to a hydrophilic moiety in which case Yb represents a single bond.

The length of the rigid moiety Ya—φ—Yb is an important aspect of this invention and is defined to be at least 10 Å as measured from the centers of the divalent coupling groups Ya and Yb. In the case in which Yb represents a bond, the length is measured from the first atom in the hydrophilic moiety. Since it is impossible to actually measure bond length between atoms practically, in accordance with this invention the length is estimated based on principles which are scientifically recognized and established in the concerned art, such as cumulation of mean bond distance between atoms, approximation by molecular model, or approximation by calculation of potential energies.

Cn in formula (I) can be any conventional hydrophobic group and is basically an alkyl group having n carbon atoms in its main chain wherein n is an integer of 4 to 24, preferably 6 to 18. These alkyl groups may be partially interrupted with double bonds, alicyclic groups, —CF$_2$—,

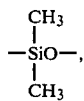

—CONH—, —O—, —NH— or the like. Examples of Cn moieties include C$_{10}$H$_{21}$, C$_{12}$H$_{25}$, C$_{14}$H$_{29}$, C$_{16}$H$_{33}$, C$_{18}$H$_{37}$—,

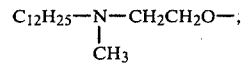

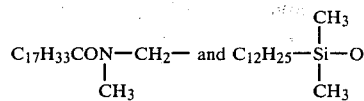

to the extent the average parameter of hydrophobic property is not less than 0.3/Å.

Cm in formula (I) is basically a methylene chain $-(CH_2)_m-$, the number m being preferably in the range from 0 to 12. Whem m is 0 the Cm moiety is not present. Hence, the term "in the hydrophobic chain" as used herein means the rigid moiety is located in the surfactant between two hydrophobic chains (Cn and Cm) or between a hydrophobic chain (Cn) and a hydrophilic group (X).

The hydrophilic group X in the formula can be selected from any of the hydrophilic groups which are well known in the art of conventional surfactants. Representative examples of hydrophilic groups are sulfonates; ammonium salts; carboxylates, sulfonium salts; phosphates, phosphonium salts; polyethers such as polyethylene glycol and polypropylene glycol; polyols including saccharide residues such as sorbitan and saccharose; and ampholytic ions such as N$^+$—N$^-$ which may be used alone or in combination.

This invention also includes structures of the formula (II) below wherein the hydrophobic terminal Cn is shared by two rigid group containing moieties. The structure of the formula (II) is equivalent to two surfactants containing the requisite rigid groups sharing a common hydrophobic moiety.

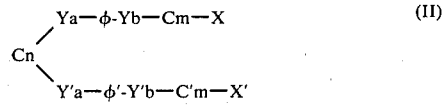

wherein Y'a, Y'b, C'm, X' and φ' are the same meaning as Ya, Yb, Cm, X and φ defined in the formula (I), respectively, and Y'a and Ya, Y'b and Yb, C'm and Cm, X' and X and φ' and φ each may be the same or different.

The aggregate of this invention is characterized by its stability at low surfactant concentrations. Unlike the labile lamellar structure formed with high concentrations of a conventional surfactant, the aggregate of this invention provides and retains a stable lamellar structure, a superimposed lamellar structure, a vesicular discus or a strand-like structure comprising such lamellar structures, which remains stable in structure and shape at concentration of about $10^{-2}$ to $10^{-7}$ M which is lower than the critical micelle concentration (CMC) of conventional surfactants, and even when concentrated or when the solvent is removed (dry). At concentrations higher than the CMC the aggregate of this invention, unlike the spherical miscelle formed by conventional surfactants, is composed of a tough structure providing a high degree of constraint between the constituent molecules. Furthermore, most of the lamellar structures formed using the surfactant of the present invention are bilayer membranes. Needless to say, these features are effectively used in selective permeation or retention of a substance as well as in acceleration or deceleration of a chemical reaction.

While the stability of the structure of this invention and its formation of a tough layer structure as well as a bilayer membrane may be verified in various manners, it is most common to use an electron microscope for direct observation, as described in T. Kunitake and Y. Okahata, J. Am. Chem. Soc., 99, 3860 (1977) and other papers by the inventors.

Direct observation under an electron microscope of the structure of this invention reveals a layer structure wherein adjacent layers are separated by a distance ranging from about 20 to 200 Å as well as molecular aggregate whose interlayer distance is on the order of several hundred Angstroms. The stability of these structures in solution and high degree of constraint resulting in a tough structure can be confirmed by the broadened peaks in an NMR spectrum.

Having these characteristics, the structure of this invenion exhibits various effective entrapping actions by virtue of its table layer structure, or it exhibits selective permeation through the layerwise structure or a vesicle composed thereof. Thus, the industrial applicability of this invention covers a wide spectrum ranging from chemical reactions, separation of various substances, conversion of energy, recording of information, conversion of information stabilization of substances, surface-protection, surface modifications or surface-treatments of polymers and inorganic solids, up to control of absorption and release of a substance.

The molecular aggregate having an ordered structure of the present invention can generally be prepared by dissolving one or more of the surfactans having the rigid moiety in an aqueous or non-aqueous solvent, optionally by applying physical means such as irradiation with supersonic waves, to thereby produce a layer structure, a bilayer structure, a multilayer structure, vesicle or a strand-like structure. As the solvent, an aqueous based solvent such as water is preferably used. The aqueous based solvent may contain, e.g., organic solvents, bases, acids, a pH buffer, metal ions, etc. Further, additional components such as synthetic polymers, natural polymers, lipids, low molecular organic compounds, conventional cationic, anionic, nonionic, or ampholytic surfactants can further be added in an amount that does not decompose the aggregate. Examples of the synthetic polymers include polyacrylic acids, polymaleic acids, copolymers of maleic acid and a vinyl monomer, polymers of vinylpyridine or copolymers with a vinyl monomer, or cationic polymers thereof, polymers of acrylamide or vinylpyrrolidone or copolymers with a vinyl monomer, polyamino acids, polyamides, polyethylene glycols, oxyethylene-oxypropylene block polymers, methyl cellulose, etc. Examples of the natural polymers include protein, gelatin, starch, gum arabic, nucleic acid, etc. Examples of the lipid include phospholipids, diollipids, sphingolipids, etc. Examples of the low molecular organic compounds include cholesterol, bile acid, stearoids (e.g., estrogen), dyes, terpenes, saccharides, aliphatic hydrocarbons, aromatic hydrocarbons, amino acid, vinyl monomers, etc. A conventional surfactant can be mixed up to 50 wt% with the surfactant of the present invention. Examples of the conventional surfactant include sodium dodecylbenzenesulfonate, trimethylcetylammonium chloride, sodium salts of higher fatty acids, polyethylene glycol nonylphenyl ether, etc.

The aggregate is used in the form of dispersion in or out of a liquid medium or solid matrix.

This invention is now described in greater detail by reference to the following examples which are given for illustrative purposes only and are by no means meant to limit the scope of this invention.

EXAMPLES 1 to 6

In Examples 1 to 6, diphenyl azomethine surfactants were synthesized, from which compounds represented by the formula (III) which are abbreviated by the formula (IV) wherein n and m refer to the number of carbon atoms in the hydrophobic chains were prepared. Details of the resulting compounds are set forth in Table 1 which will be given hereinafter.

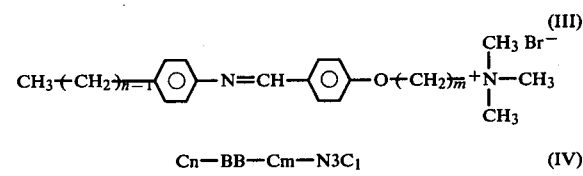

$$C_n - BB - C_m - N3C_1 \quad (IV)$$

trimethyl-ammoniumalkyleneoxy)benzaldehyde bromide synthesized in the manner described below was refluxed for 0.5 to 1 hour in the presence of a small amount of acetic acid using ethanol as a solvent, and the resulting precipitate was recrystallized from ethanol two to four times. The yield was from 50 to 80%.

Preparation of p-(ω-trimethylammoniumbutoxy)benzaldehyde bromide

To a solution of 2.3 g of metallic sodium in 200 ml of anhydrous alcohol were added simultaneously 64.8 g of 1,4-dibromobutane and 12.4 g of p-hydroxybenzaldehyde, and the resulting mixture was heated under reflux for 4 hours. After reaction, the mixture was poured into ice water and the oily product which precipitated was extracted with chloroform, followed by purification to yield 15 g (58%) of p-(ω-bromobutyloxy)benzaldehyde boiling at 145°–147° C. under 0.01 mm Hg. A solution of 15 g of the product in 80 ml of ethanol was reacted with 106 g of a 30% aqueous trimethylamine solution in an ampule at 100° C. for 38 hours. After the reaction, the solvent was distilled off and the precipitated solid was recrystallized from ethanol to yield 16 g (86%) of the intended product having a melting point of 201° C.

NMR Spectrum (in $d_6$ DMSO):
$\delta = 3.1$ ppm (s) 9H, $N^+$—$CH_3$; $\delta = 7.2$ (d), 7.9 (d) 4H, phenyl; $\delta = 10.0$ (s) 1H, aldehyde.

The same procedure was used to prepare each of the compounds of formula (III).

Depending on its molecular weight (so as to make the concentration in mol/l constant), 180 to 260 mg each compound (III) was suspended in 40 ml of distilled water and sonicated with a Branson Sonifier 185 (produced by Branson Instrument Co.) for 5 to 15 minutes to provide a 10 mM homogeneous aqueous solution. A mixture of 1 ml of the solution and 1 ml of 2% aqueous uranyl acetate solution was stirred under sonication for about 20 seconds, cooled in an ice bath for 30 minutes, placed on a carbon membrane, dehydrated in a desiccator under vacuum, and observed under a Hitachi Electron Microscope H-500 (×150,000 to 300,000) at an acceleration voltage of 75 to 100 kv, providing the electron micrographs of FIGS. 2 through 7.

TABLE 1

| Example No. | Abbr. for Compounds | m.p. (°C.) | Elemental Analysis (calculated values in parentheses) C | H | N | Structure | FIG. No. | NMR Spectral No. |
|---|---|---|---|---|---|---|---|---|
| 1 | $C_{12}$—BB—$N^+3C_1$ | 152–3 | 66.99 (66.53) | 8.92 (8.91) | 5.48 (5.54) | vesicular | 2 | 1 |
| 2 | $C_7$—BB—$N^+3C_1$ | 165–6 | 66.05 (66.19) | 7.99 (7.91) | 6.67 (6.71) | " | 3 | 2 |
| 3 | $C_{12}$—BB—$C_4$—$N^+3C_1$ | 120 | 66.18 (66.09) | 9.77 (9.93) | 4.84 (4.82) | " | 4 | |
| 4 | $C_7$—BB—$C_4$—$N^+3C_1$ | 145 | 67.76 (66.26) | 8.85 (8.38) | 5.83 (5.73) | " | 5 | |
| 5 | $C_{12}$—BB—$C_{10}$—$N^+3C_1$ | 128 | 73.89 (70.92) | 10.40 (9.80) | 4.51 (4.35) | " | 6 | |
| 6 | $C_7$—BB—$C_{10}N^+3C_1$ | 195 | 68.87 (69.10) | 9.31 (9.25) | 4.86 (4.89) | " | 7 | |

From a molecular model of the compound prepared in Example 1 the rigid moiety was estimated to be about 12.4 Å long as follows:

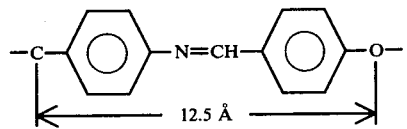

To prepare each compound (III), an equimolar mixture of the corresponding p-alkyl aniline and p-(ω-

EXAMPLES 7 TO 12

In Examples 7 to 12, diphenyl surfactants of the formula (V) were prepared by varying X' of the formula. The procedure of Example 1 was repeated to provide an aggregate of each compound. Detailed characteristics of each compound are set forth in Table 2 which will be given hereinafter.

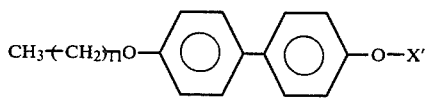

(V)

The compound (V) was prepared by the following reaction scheme:

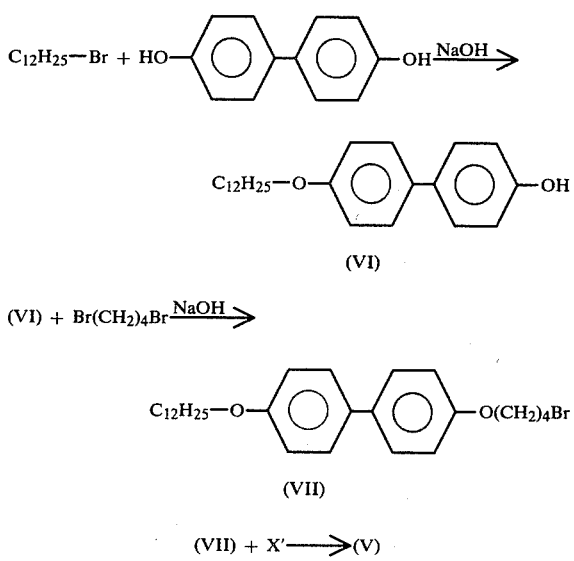

Preparation of

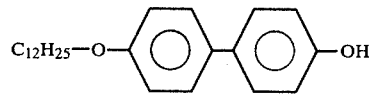

(VI)

A mixture of 55.8 g of 4,4'-dihydroxybiphenyl and 24.9 g of dodecyl bromide was heated under reflux for 5 hours in the presence of 4 g of sodium hydroxide and 300 ml of ethanol. After the reaction, the mixture was cooled to room temperature upon which a white crystal precipitated. Recrystallization from ethyl acetate yielded 22 g (62%) of the intended product melting at 110° to 135° C.

Preparation of

(VII)

A mixture of 17.7 g of the compound (VI) and 32.4 g of 1,4-dibromobutane was heated under reflux for 6 hours in the presence of 2 g of sodium hydroxide and 200 ml of ethanol. After the reaction, the mixture was poured into distilled water until a white solid precipitated. Recrystallization of the precipitate from ethyl acetate yielded 20 g (82%) of the intended product melting at 95° to 97° C.

NMR Spectrum (in CDCl$_3$):

$\delta=0.9$ (s) 3H, —CH$_3$; $\delta=1.3$ (s) 24H, —CH$_2$—; $\delta=3.5$ (m) 2H, Br—CH$_2$—; $\delta=4.0$ (m) 4H, —O—CH$_2$; $\delta=6.9$–7.5 (m) 8H aromatic H.

In Example 7, a mixture of the compound (VII) and trimethylamine was heated under reflux in ethanol in a glass ampoule at 100° C. for 48 hours and the reaction mixture was then recrystallized first from ethyl acetate, then from benzene/ethanol, to yield 63% of a product which was identified by NMR.

IN Example 8, a mixture of the compound (VII) and N-methyl glucan was heated under reflux in ethanol in the presence of sodium carbonate for 50 hours. The reaction product was obtained in a yield of 89% by recrystallization from ethanol and subjected to further reaction in the presence of methyl bromide in an ampoule at 100° C. for 80 hours, followed by recrystallization from ethanol to provide the end compound.

In Example 9, a mixture of the compound (VII) and N,N-dimethyl hydrazine was heated under reflux for 16 hours in a solvent mixture comprising equal volumes of ethanol and benzene. The reaction product was obtained in a yield of 80% by recrystallization from ethanol and reacted under reflux with acetyl chloride in benzene for 2 hours. The solvent was distilled off, the residue was suspended in water, mixed with 10% aqueous sodium hydroxide solution to obtain a pH in the range from 10 to 11, further reacted under stirring for 2 hours, and the reaction system was extracted with chloroform. Following distillation of chloroform, a white solid recrystallized from ethanol to yield 67% of end product.

In Examples 10 and 11, 2.8 g of the compound (VII) was reacted with 4.0 g and 8.0 g of ethylene oxide, respectively, in the presence of sodium hydroxide in an autoclave at 120° to 160° C. for 2.5 hours. The purified reaction product was found to contain a single compound by Jatron synchrography. Elemental analysis and NMR technique gave the same value for the addition ethylene oxide unit.

In Example 12, the compound (VII) was reacted with phosphorous oxytrichloride by heating under reflux in the presence of benzene for 3 hours. The reaction mixture was recrystallized from ethanol to provide the intended product at a yield of 48%.

TABLE 2

| Example No. | X' | m.p. (°C.) | Elemental Analysis (calculated values in parentheses) | | | | FIG. No. |
| --- | --- | --- | --- | --- | --- | --- | --- |
| | | | C | H | N | Structure | |
| 7* | (CH$_2$)$_4$—$^+$N(CH$_3$)$_3$ Br$^-$ | 160 | 66.86 (66.78)** | 9.09 (9.16)** | 2.57 (2.51)** | vesicule containing cholesterol | 8 |

TABLE 2-continued

| Example No. | X' | m.p. (°C.) | Elemental Analysis (calculated values in parentheses) C | H | N | Structure | FIG. No. |
|---|---|---|---|---|---|---|---|
| 8 | $\begin{array}{c}\text{CH}_3 \quad \text{Br}^-\\ |\\ (\text{CH}_2)_4{}^+\text{N}-\text{CH}_2(\text{CH})_5\text{H}\\ |\quad\quad\quad |\\ \text{CH}_3\quad\text{OH}\end{array}$ | — | 62.30 (61.89) | 8.90 (8.60) | 2.12 (2.00) | lamellar | 9 |
| 9 | $\begin{array}{c}\text{CH}_3\\ |\\ (\text{CH}_2)_4{}^+\text{N}-\text{N}^-\text{COCH}_3\\ |\\ \text{CH}_3\end{array}$ | 80 | 72.29 (72.45) | 9.82 (9.43) | 4.26 (4.28) | vesicular | 10 |
| 10 | $(\text{CH}_2.\text{CH}_2\text{O})_{10}\text{H}$ | — | n was found to be 11.9 | | | lamellar | 11 |
| 11*** | $(\text{CH}_2.\text{CH}_2\text{O})_{20}\text{H}$ | — | n was found to be 20.1 | | | sperical*** | 12 |
| 12 | $-\text{PO}_3{}^=$ | 120 | 67.22 (66.36)**** | 8.57 (8.06)**** | — | discuss lamellar | 13 |

*An equal amount of cholesterol was used to form the structure.
**Calculated for ½H₂O.
***A 10-times volume of liquid paraffin was used to form the structure.
****Calculated for C₂₄H₃₅O₅P.

EXAMPLE 13

A compound of the following formula was prepared in the following manner.

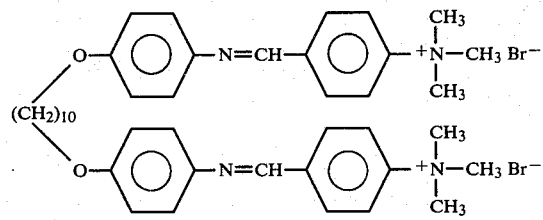

An equimolar mixture of p-trimethylammoniumbenzaldehyde bromide and 1,10-bis(p-aminophenoxy)decane synthesized in the manner described below was refluxed for 1 hour in the presence of a small amount of acetic acid using ethanol as a solvent, and the resulting precipitate was recrystallized from ethanol three times to yield 50 to 80% of a pale yellow grained crystal having a melting point of 195° to 200° C. The structure of the crystal was confirmed by NMR spectrum.

Elemental Analysis (calculated for C₄₂H₅₆N₄O₂Br₂.H₂O):

C 61.28 (61.02); H 7.18 (7.02); N 6.51 (6.78).

(1) Preparation of p-trimethylammoniumbenzaldehyde bromide 25 g (0.17 mole) of p-dimethylaminobenzaldehyde was dissolved in 100 ml of benzene and the mixture was charged in a glass ampule. After 60 ml (0.63 mole) of methyl bromide was added to the mixture with cooling with liquid nitrogen, the glass ampule was sealed and the reaction was carried out at 90° C. for 100 hours. After the reaction, the ampule was opened and the resulting yellow precipitate was filtered and recrystallized from ethyl acetate to obtain a pale yellow acicular crystal having a melting point of 208° to 210° C. at a yield of 31 g (81%).

(2) Preparation of 1,10-bis(p-aminophenoxy)decane 30 g (0.1 mole) of 1,10-dibromodecane and 38 g (0.25 mole) of p-hydroxyacetanilide were heated under reflux for 8 hours in the presence of 12 g of NaOH using ethanol. After the reaction, the resulting mixture was poured into ice water and the precipitate formed was collected, followed by washing with heated ethanol. The remaining brown crystal without purification was added in a mixed solvent of 100 ml of conc. HCl and 200 ml of ethanol and the system was heated under reflux for 2 hours. A solid remained after removing the solvent under reduced pressure which was dissolved in 2 l of ice water, and a 20% NaOH aqueous solution was added thereto to neutralize. The thus-precipitated solid was collected and recrystallized from ethanol to a pale brown grained crystal having a melting point of 70° to 71° C. at a yield of 18 g (51%). The crystal was identified as 1,10-bis(p-aminophenoxy)decane from its NMR spectrum and IR spectrum.

Figure 14:
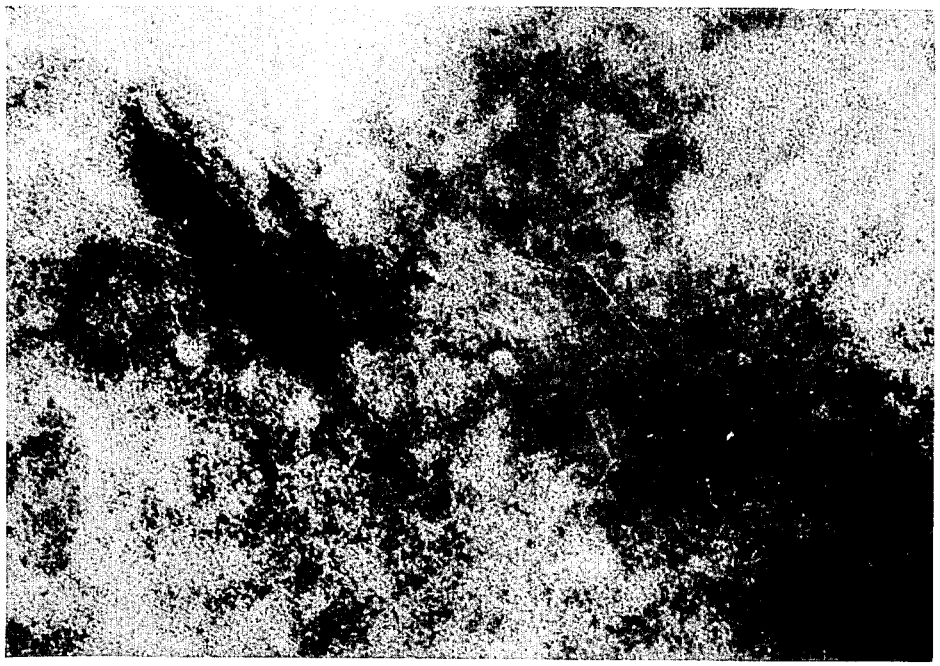

5 mg of the thus obtained compound of the above formula was dispersed in 1 ml of distilled water in the same manner as in Examples 1 to 6. The electron micrograph appears in FIG. 14.

EXAMPLE 14

A compound of the folllowing formula was prepared as set forth below.

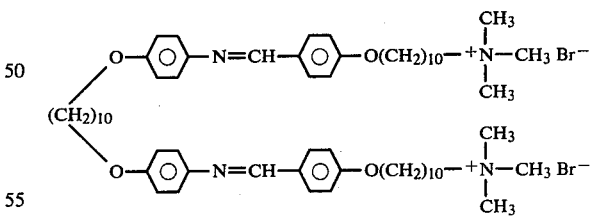

m.p.: 245-250° C.

An equimolar mixture of p-(ω-trimethylammoniumdodecyloxy) benzaldehyde bromide as prepared in Examples 1 to 6 and 1,10-bis(p-aminophenoxy)decane as prepared in Example 13 was refluxed for 1 hour in the presence of a small amount of acetic acid using ethanol as a solvent. The thus-obtained precipitate was recrystallized from ethanol three times to obtain a brown powder having a melting point of 245° to 250° C. The structure of the powder was confirmed by NMR spectrum.

Elemental Analysis (calculated values for $C_{62}H_{96}N_4O_4Br_2 \cdot 2H_2O$):

C 64.66 (64.35); H 8.75 (8.65); N 4.92 (4.84).

Figure 15:

5 mg of the thus obtained compound was dispersed in 1 ml of the distilled water in the same manner as in Examples 1 to 6. The electron micrograph appears in FIG. 15.

EXAMPLE 15

2.3 g (5 mmoles) of cholesterol chloroacetate (produced by Tokyo Kasei Co.) in 20 ml of triethylamine was heated under reflux for 20 hours. The reaction solution was subjected to distillation under reduced pressure to obtain a solid which was subsequently recrystallized from a mixture of ethanol and water to obtain cholesterol-(α-triethylammonium)acetate chloride having the melting point of 110° to 130° C. at a yield of 2 g (68%). The structure of the compound was confirmed by NMR spectrum. 10 g of the thus-obtained compound and 10 mg of cetyl trimethylammonium bromide were dispersed in 2 ml of distilled water in the same manner as in Examples 1 to 6. The dispersion was examined under an electron microscope and a lamellar structure was observed.

EXAMPLE 16

This example illustrates a compound of the following formula (VIII):

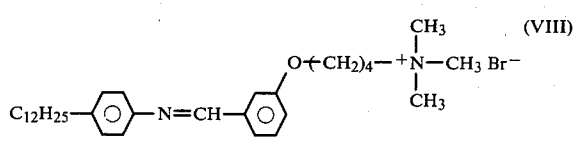

The length of the rigid moiety was estimated by molecular model to be about 11.3 Å long as follows:

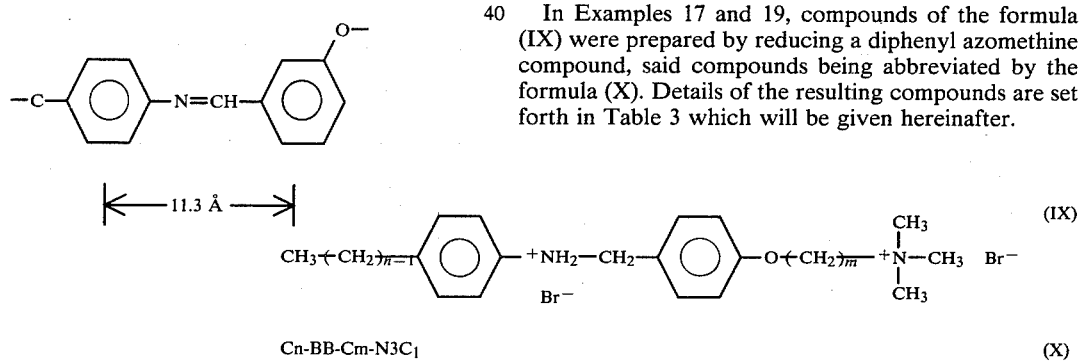

Cn-BB-Cm-N3C₁

Preparation of Compound (VIII)

An equimolar mixture of p-dodecyl aniline and m-(ω-trimethylammoniumbutoxy)benzaldehyde bromide synthesized in the manner described below was refluxed for 0.5 to 1 hour in the presence of a small amount of acetic acid using ethanol as a solvent, and the resulting precipitate was recrystallized from ethanol two to four times to yield 60% of a pale yellow acicular crystal melting at 79° to 103° C.

Elemental Analysis (calculated values in parentheses):

C 66.87 (66.53); H 9.31 (9.25); N 4.93 (4.85).

Preparation of m-(ω-trimethylammoniumbutoxy)benzaldehyde bromide

To a solution of 2.3 g of metal sodium in 200 ml of absolute alcohol were added simultaneously 64.8 g of 1,4-dibromobutane and 12.4 g of m-hydroxybenzaldehyde, and the resulting mixture was heated under reflux for 4 hours. After reaction, the mixture was poured into ice water, and the precipitated oily product was extracted with chloroform, followed by purification which yielded 14 g (54%) of m-(ω-bromobutyoxy)benzaldehyde boiling at 129°–134° C. under 0.003 mmHg. A solution of 14 g of the product in 80 ml of ethanol was reacted with 99 g of 30% aqueous trimethylamine solution in an ampule at 100° C. for 38 hours. After the reaction, the solvent was distilled off and the precipitated solid was recrystallized from ethanol to yield 14.5 g (84%) of the intended product melting at 143°–146° C.

Figure 16:
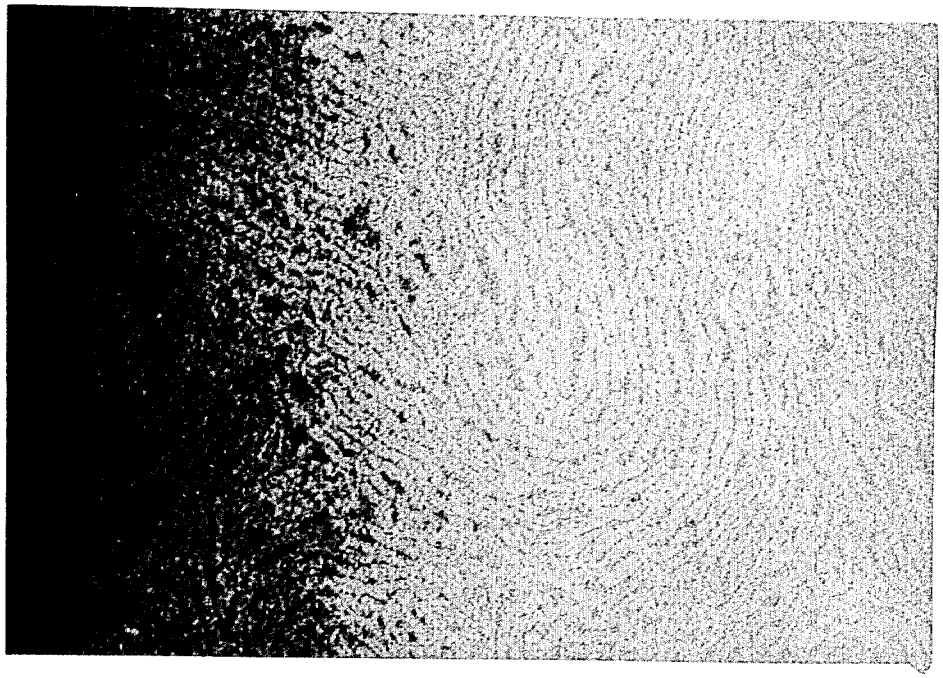

A 224 mg sample of compound (VIII) was suspended in 40 ml of distilled water and sonicated by Branson Sonifier 185 for 5 to 15 minutes to provide a 10 mM homogeneous aqueous solution. A mixture of 1 ml of the solution and 1 ml of 2% aqueous uranyl acetate solution was stirred under sonication for about 20 seconds, cooled in an ice bath for 30 minutes, placed on a carbon membrane, dehydrated in a desiccator under vacuum, and observed under a Hitachi Electron Microscope H-500 (×300,000) at an acceleration voltage of 75 to 100 kv, providing an electron micrograph of FIG. 16, which clearly indicates the presence of a lamellar structure.

EXAMPLES 17 TO 19

In Examples 17 and 19, compounds of the formula (IX) were prepared by reducing a diphenyl azomethine compound, said compounds being abbreviated by the formula (X). Details of the resulting compounds are set forth in Table 3 which will be given hereinafter.

The compound (IX) can be obtained as an HBr salt by reducing with $NaBH_4$ in ethanol a diphenyl azomethine compound synthesized from the corresponding p-alkyl aniline and p-(ω-trimethylammoniumalkyleneoxy)benzaldehyde bromide which was synthesized in the same manner as in Example 16.

Figure 17:
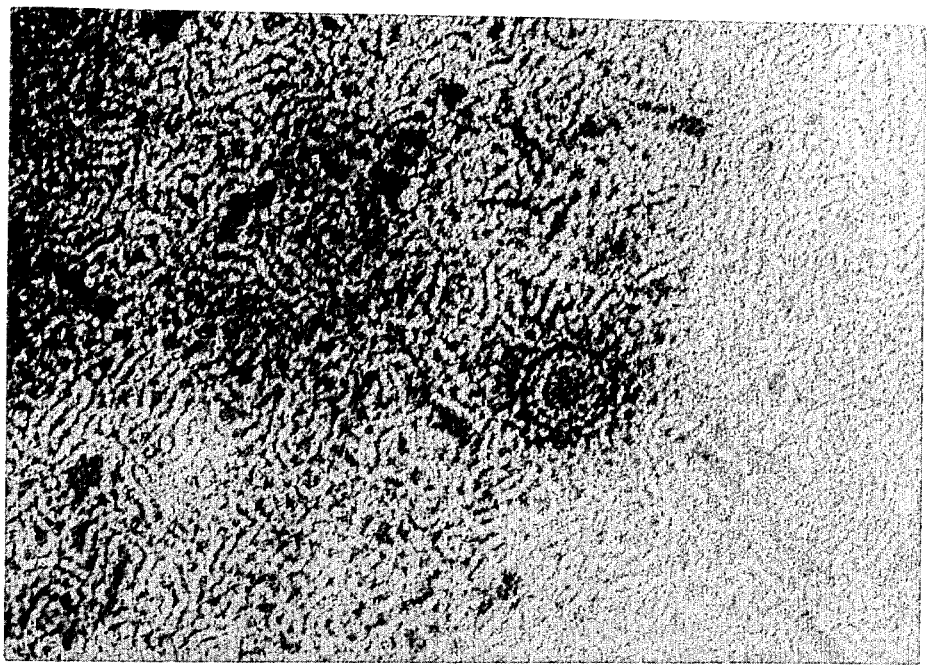
Figure 18:
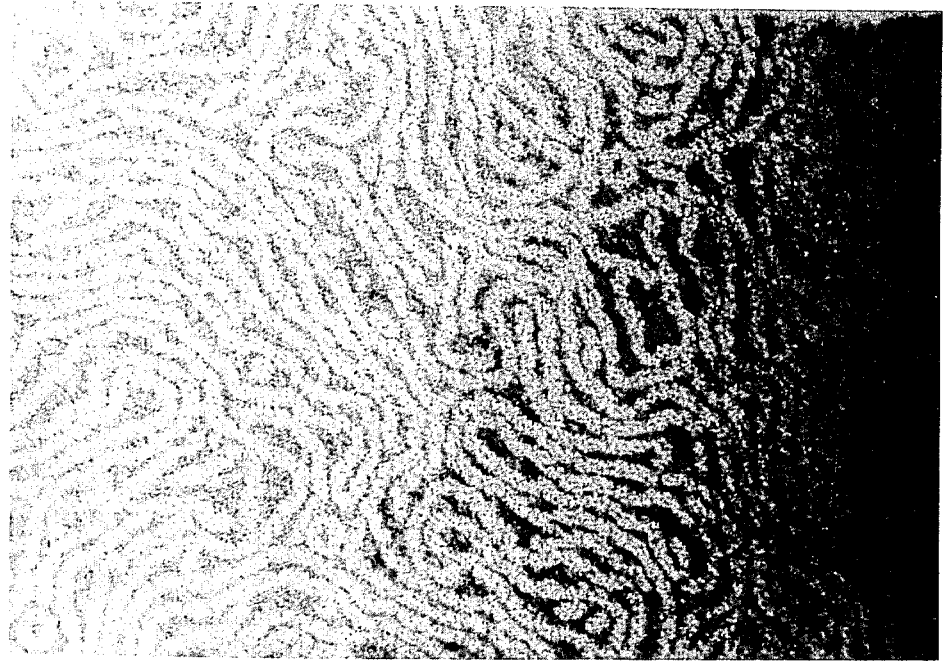
Figure 19:
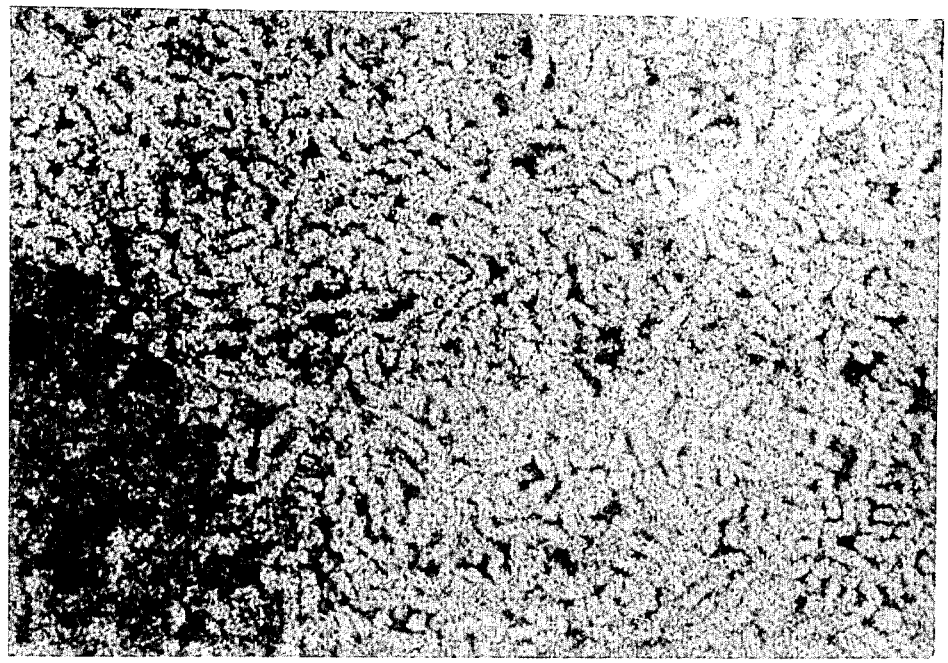

A neutralized compound (IX) was suspended in distilled water in the same manner as in Example 16 and observed under an electron microscope which showed the formation of an aggregate. Accompanying FIGS. 17 TO 19 are electron micrographs of the compounds prepared in Examples 17 to 19.

TABLE 3

| Example No. | Abbr. for Compound (molecular formula in parentheses) | m.p. (°C.) | Elemental Analysis (calculated values in parentheses) C | H | N | Structure | FIG. No. |
|---|---|---|---|---|---|---|---|
| 17 | $C_{12}$—BB—$N^+3C_1$ (reduced form) ($C_{28}H_{46}N_2Br_2 \cdot 8H_2O$) | 127–134 | 47.03 (47.06) | 7.03 (8.74) | 3.91 (3.92) | lamellar | 17 |
| 18 | $C_{12}$—BB—$C_4$—$N^+3C_1$ (reduced form) ($C_{32}H_{54}N_2OBr_2 \cdot 7H_2O$) | 185–187 | 49.74 (50.00) | 7.03 (8.92) | 3.52 (3.64) | lamellar | 18 |
| 19 | $C_{12}$—BB—$C_{10}$—$N^+3C_1$ (reduced form) ($C_{38}H_{60}N_2OBr_2 \cdot 6H_2O$) | 83–85 | 55.11 (54.67) | 8.43 (9.42) | 3.36 (3.36) | loose lamellar | 19 |

EXAMPLES 20 TO 22

In Examples 20 to 22, compounds of the formula (XI) were synthesized from their respective starting materials.

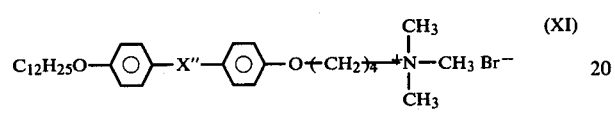
(XI)

wherein —X″— represents —O—,

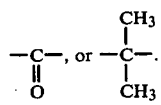

Compound (XI) was synthesized by the following reaction scheme:

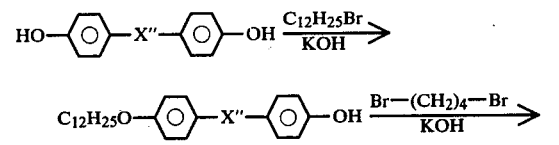

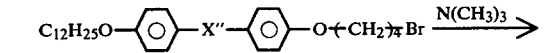

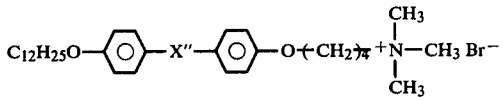

Figure 20:
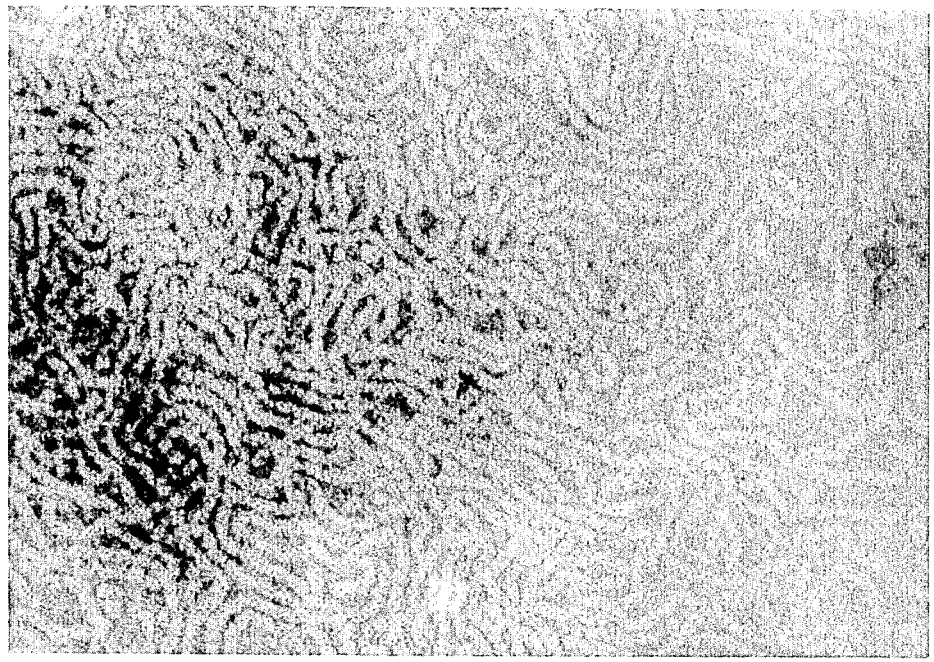
Figure 21:
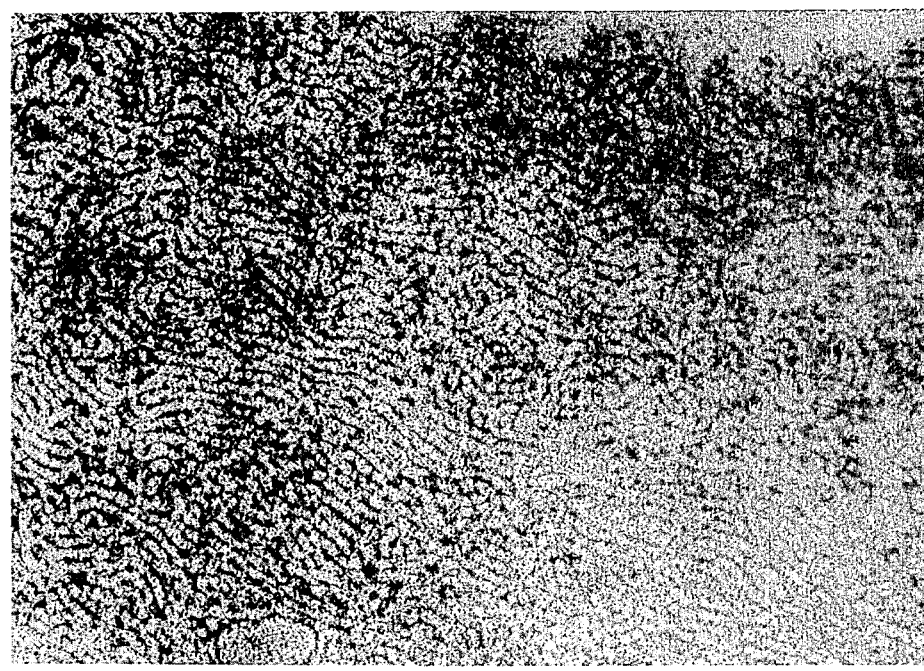
Figure 22:
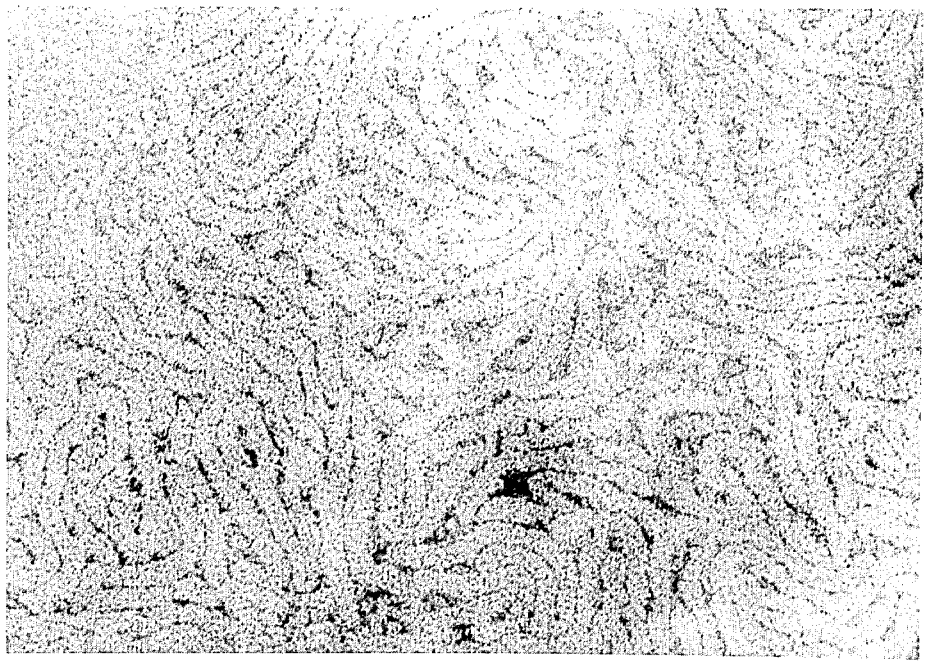

A mixture of 0.3 mole of the corresponding dihydroxy compound and 0.1 mole of dodecyl bromide was heated under reflux for 5 hours in 300 ml of ethanol in the presence of 0.1 mole of potassium hydroxide. A mixture of 0.05 mole of the reaction product and 0.15 mole of 1,4-dibromobutane was heated under reflux for 6 hours in the presence of 0.05 mole of potassium hydroxide in 200 ml of ethanol. The reaction product was mixed with trimethylamine and heated in ethanol in a glass ampule at 100° C. for 48 hours to thereby provide a compound of the formula (XI). Table 4 below shows the melting points of the intermediate products obtained during the preparation of the compound (XI). Table 5 below sets forth details of the resulting compounds (XI). Depending on its molecular weight, 4 to 5 mg of the compound (XI) was dispersed in 1 ml of distilled water and 1 ml of 2% aqueous solution of uranyl acetate was added thereto. The electron micrographs are given in FIGS. 20 to 22, respectively.

TABLE 4

Melting Points
Rigid Moiety

| —X— | HO—⟨O⟩—X—⟨O⟩—OH | $C_{12}H_{25}$—O—⟨O⟩—X—⟨O⟩—OH | $C_{12}H_{25}$—O—⟨O⟩—X—⟨O⟩—O(CH$_2$)$_4$—Br |
|---|---|---|---|
| —O— | 166–168 | 93–95 | 75–82 |
| —C(CH$_3$)$_2$— | oily substance | oily substance | oily substance |
| —C(=O)— | 221–222 | 85–94 | 93–94 |

TABLE 5

| Example No. | Abbr. for Compounds (molecular formula in parentheses) | m.p. (°C.) | Elemental Analysis (calculated values in parentheses) C | H | N | Structure | FIG. No. |
|---|---|---|---|---|---|---|---|
| 20 | $C_{12}$—B—O—B—$C_4$—$^+N3C_1$ ($C_{31}H_{50}O_3NBr \cdot H_2O$) | waxy | 64.22 (63.90) | 8.96 (8.82) | 2.54 (2.40) | lamellar (strand) | 20 |
| 21 | $C_{12}$—B—C(CH$_3$)$_2$—B—$C_4$—$^+N3C_1$ | waxy | 67.01 (67.08) | 9.44 (9.60) | 2.35 (2.30) | lamellar | 21 |

TABLE 5-continued

| Example No. | Abbr. for Compounds (molecular formula in parentheses) | m.p. (°C.) | Elemental Analysis (calculated values in parentheses) | | | Structure | FIG. No. |
|---|---|---|---|---|---|---|---|
| | | | C | H | N | | |
| 22 | $C_{12}$—B—C(=O)—B—$C_4$—$^+N3C_1$ | 123–130 | 66.51 (66.67) | 8.56 (8.68) | 2.48 (2.43) | lamellar (strand) | 22 |

EXAMPLE 23

The procedure of Example 16 was repeated to synthesize a compound of the formula (XII) from m-dodecyloxyaniline and m-(ω-trimethylammoniumbutoxy)benzaldehyde bromide, the compound melting at 60°–75° C.

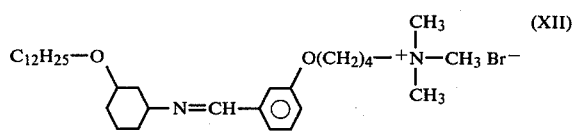

(XII)

The compound (XII) was more dispersible in water than the p,p′-diphenyl azomethine compound, and upon sonication, it turned to a transparent aqueous solution having a concentration of about 10 mM.

Figure 23:
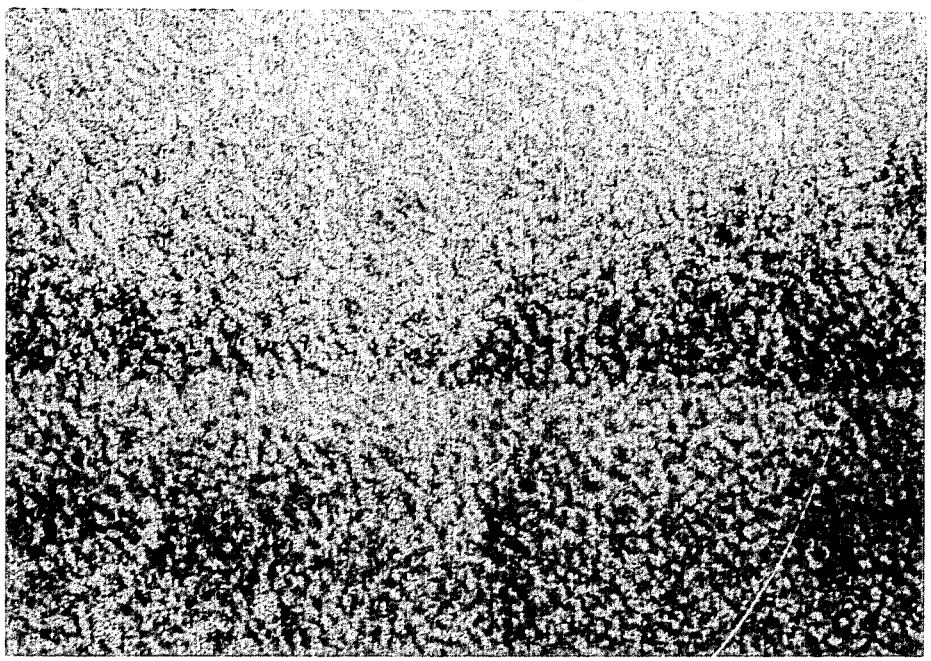

The compound was examined under an electron microscope (×300,000). The electron micrograph of FIG. 23 shows a considerably irregular aggregate.

EXAMPLE 24

Figure 24:
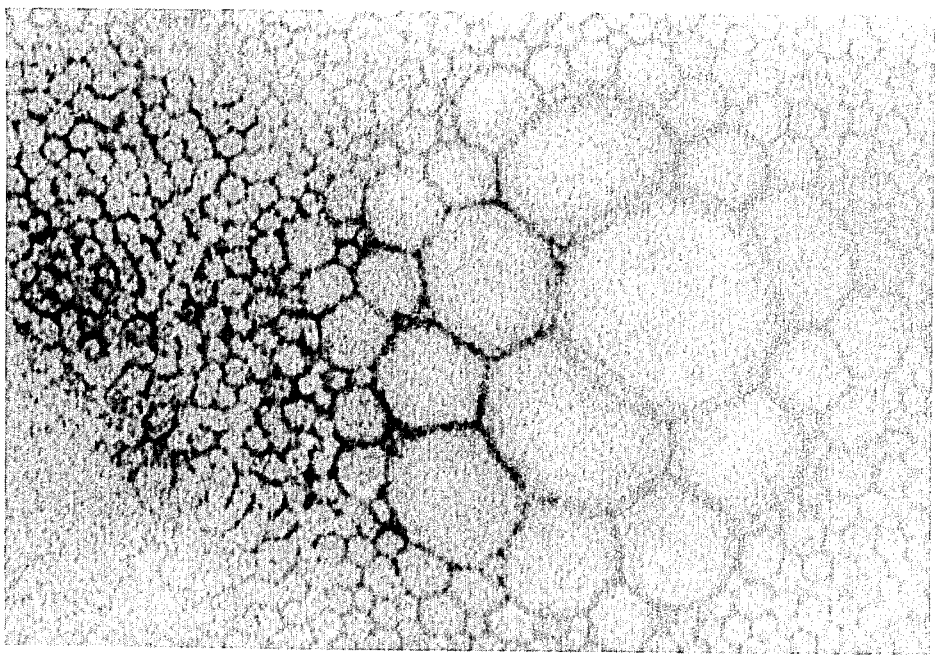

A mixture of the compound $C_{12}$—BB—$C_4$—$^+N3C_1$ prepared in Example 18 and liquid paraffin in equal weights was poured into distilled water and sonicated to provide a stable emulsion comprising globules of a size in the range from 200 to 2,000 Å as shown in FIG. 24.

EXAMPLE 25

Figure 25:
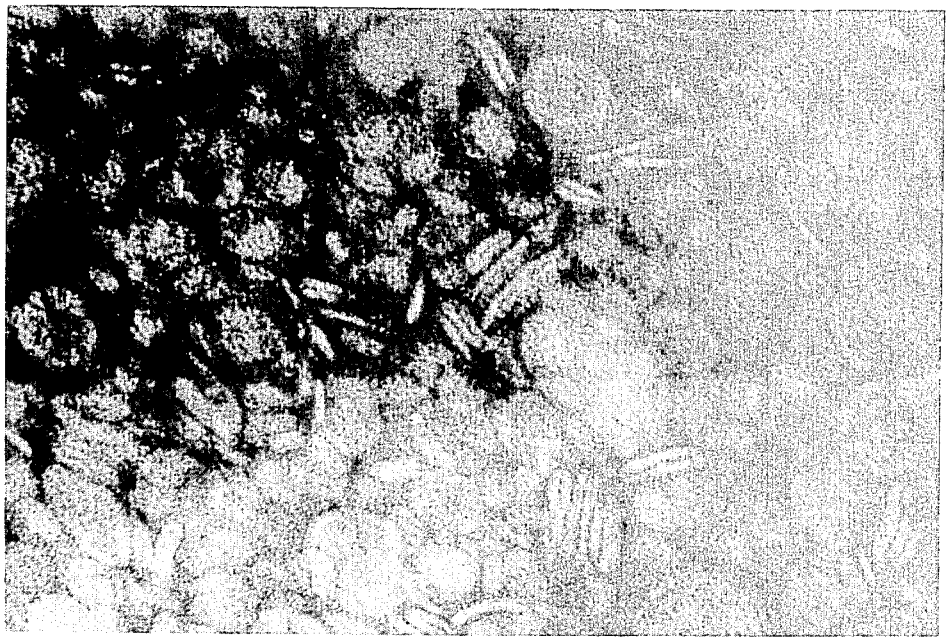

A compound of the formula (XIII) prepared from p-dodecyloxyaniline and m-(ω-trimethylammoniumbutoxy)benzaldehyde bromide was mixed with cholesterol in a weight ratio of 1:0.5, and the mixture was dissolved in distilled water. Electron microscopic observation (×300,000) of the solution showed the presence of many ruptured vesicles as shown in FIG. 25.

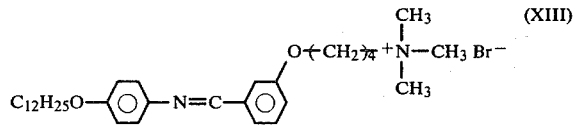

(XIII)

While the invention has been described in detail and with reference to specific embodiments thereof, it will be apparent to one skilled in the art that various changes and modifications can be made therein without departing from the spirit and scope thereof.

What is claimed is:

1. A stable molecular aggregate consisting essentially of a surfactant having an ordered structure primarily consisting of a bilayer structure as its basic structural unit, said surfactant comprising a surfactant represented by formula (I) or (II):

$$Cn-Ya-\phi-Yb-Cm-X \quad (I)$$

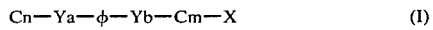

wherein Cn represents a hydrophobic moiety, Ya—φ—Yb and Ya′—φ′—Yb′ each represents a rigid moiety having a length of at least 10 Å, Ya, Ya′, Yb and Yb′ each represents a divalent coupling group, φ and φ′ each represents a rigid group capable of bonding Ya and Yb or Ya′ and Yb′, Cm and Cm′ each represents a $(CH_2)m$ group, where m is 0 or an integer of 1 to 12, and X and X′ represents a hydrophilic moiety selected from the group consisting of sulfonates, ammonium salts, carboxylates, sulfonium salts, phosphates, phosphonium salts, polyethers, polyols, and ampholytic ions.

2. The molecular aggregate of claim 1, wherein said rigid group is at least two aromatic rings condensed or bonded directly to one another or through a carbon-carbon multiple bond, a carbon-nitrogen multiple bond, a nitrogen-nitrogen multiple bond, an ester linkage, or an amide linkage.

3. The molecular aggregate of claim 1, wherein said rigid group is at least two aromatic rings coupled by two or three of single bonds.

4. The molecular aggregate of claim 1, wherein said rigid group is a three-dimensionally stabilized alicyclic condensed ring.

5. The molecular aggregate of claim 1, wherein Ya, Ya′, Yb and Yb′ represent a divalent coupling group selected from the group consisting of —$CH_2$—, —CO—, —O—, —NH—, —S—, and —$SO_2$—.

6. The molecular aggregate of claim 1, wherein Cn represents an alkyl group having 4 to 24 carbon atoms along the main chain which may be interrupted.

7. The molecular aggregate of claim 1, wherein said surfactant is dispersed in a liquid medium.

8. The molecular aggregate of claim 7, wherein said liquid medium is an aqueous based solvent.

9. The molecular aggregate of claim 1, wherein said surfactant containing said rigid moiety is present in an amount of about $10^{-2}$ to $10^{-7}$ mole per liter.

10. The molecular aggregate of claim 1, wherein said X and X′ represent a hydrophilic moiety selected from the group consisting of ammonium salts, phosphates and polyethers.

11. The molecular aggregate of claim 1, wherein said aggregate additionally comprises a component in an amount that does not decompose said aggregate, said component being selected from the group consisting of synthetic polymers, natural polymers, lipids, dyes, terpenes, saccharides, aliphatic hydrocarbons, aromatic hydrocarbons, amino acids, vinyl monomers, sodium dodecylbenzensulfonate, trimethylcetylammonium chloride, sodium salts of higher fatty acids and polyethylene glycol nonylphenyl ether.

12. The molecular aggregate of claim 11, wherein said component is selected from the group consisting of sodium dodecylbenzenesulfonate, trimethylcetylammonium chloride, sodium salts of higher fatty acids and polyethylene glycol nonylphenyl ether, and said component is mixed up to 50 wt% with said surfactant.
13. The molecular aggregate of claim 1, wherein φ and φ' are selected from groups (1)-(4) below:
Group (1)
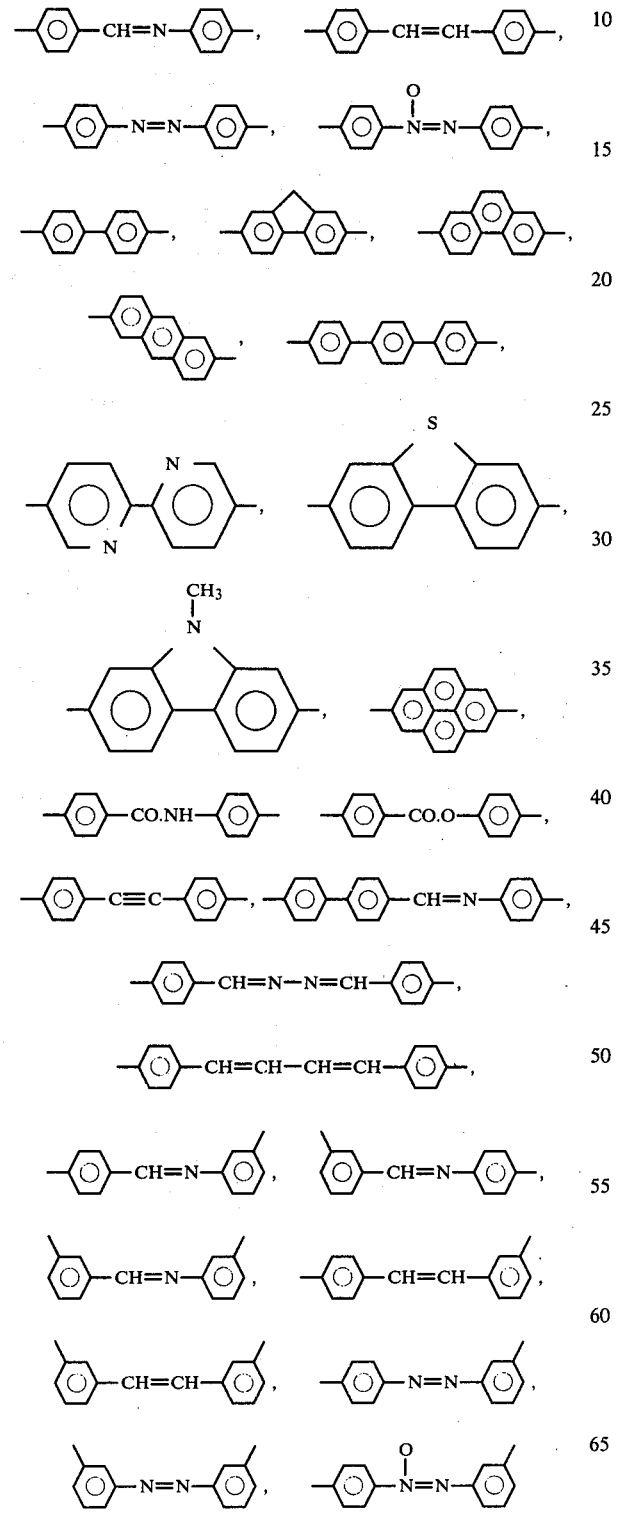
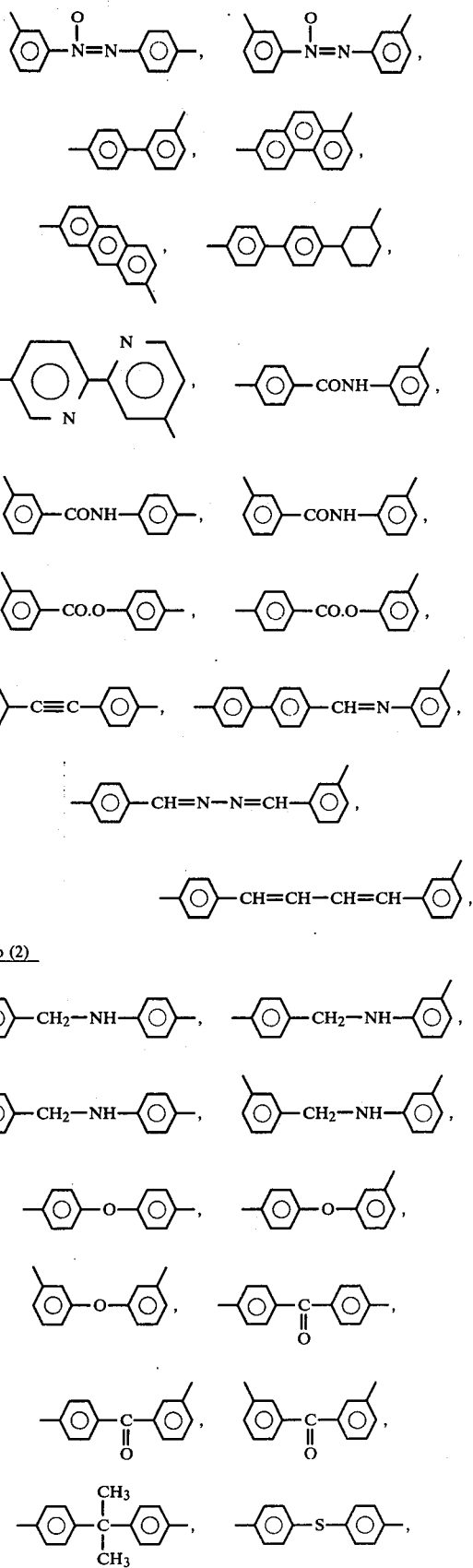

-continued

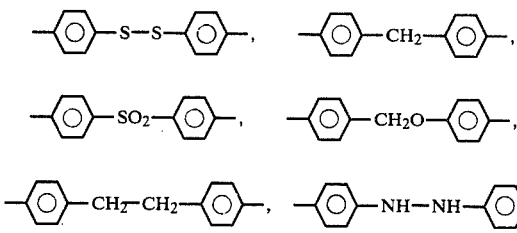

Group (3)

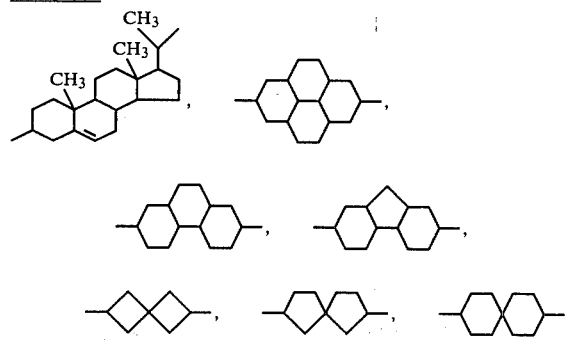

Group (4)

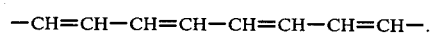

—C≡C—C≡C—, and

—CH=CH—CH=CH—CH=CH—CH=CH—.

14. The molecular aggregate of claim 1, wherein said rigid moiety provides a generally linear or parallel relation between Ya-$\phi$ and Yb-$\phi$ or between Ya'-$\phi'$ and Yb', said axes forming an angle of 20° or less.

15. The molecular aggregate of claim 1, wherein X and X' represent a hydrophilic moiety selected from the group consisting of sulfonates and sulfonium salts.

16. The molecular aggregate of claim 1, wherein X and X' represent a hydrophilic moiety selected from the group consisting of carboxylates.

17. The molecular aggregate of claim 1, wherein X and X' represent a hydrophilic moiety selected from the group consisting of phosphates and phosphonium salts.

18. The molecular aggregate of claim 1, wherein X and X' represent a hydrophilic moiety selected from the group consisting of polyols.

19. The molecular aggregate of claim 1, wherein X and X' represent a hydrophilic moiety selected from the group consisting of ampholytic ions.

20. The molecular aggregate of claim 1, wherein the surfactant is represented by formula (II).

21. A stable molecular aggregate consisting of a surfactant having an ordered structure primarily consisting of a bilayer structure as its basic structural unit, said surfactant comprising a hydrophilic moiety and a hydrophobic moiety and having in the hydrophobic moiety or between the hydrophobic moiety and the hydrophilic moiety, a rigid moiety at least 10 Å long, said surfactant being represented by the formula (I) or (II):

$$Cn—Ya—\phi—Yb—Cm—X \quad (I)$$

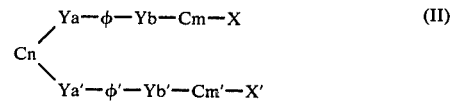

wherein Cn, Cm and Cm' represent a hydrophobic moiety, X and X' represent a hydrophilic moiety selected from the group consisting of sulfonates, ammonium salts, carboxylates, sulfonium salts, phosphates, phosphonium salts, polyethers, polyols and ampholytic ions, Ya-$\phi$-Yb and Ya'-$\phi'$-Yb' represent said rigid moiety, Ya, Ya', Yb and Yb' representa a divalent coupling group and $\phi$ and $\phi'$ represent a rigid group selected from the group consisting of (1) at least two benzene rings condensed or bonded directly to one another or through a carbon-carbon multiple bond, a carbon-nitrogen multiple bond, a nitrogen-nitrogen multiple bond, an ester linkage or an amide linkage, and (2) at least two benzene rings coupled by two or three single bonds, in which said Ya and Yb or Ya' and Yb' are bonded to said benzene rings at the 4-position thereof.

22. The molecular aggregate of claim 21, wherein said rigid group is at least two benzene rings bonded directly to one another or through a carbon-carbon multiple bond, a carbon-nitrogen multiple bond, a nitrogen-nitrogen multiple bond, an ester linkage, or an amide linkage.

23. The molecular aggregate of claim 21, wherein said rigid group is at least two benzene rings coupled by two or three single bonds.

24. The molecular aggregate of claim 21, wherein Ya, Ya', Yb and Yb' represent a divalent coupling group selected from the group consisting of —CH$_2$—, —CO—, —O—, —NH—, —S—, and —SO$_2$—.

25. The molecular aggregate of claim 21, wherein Cm and Cm' represent an alkyl group having 4 to 24 carbon atoms which may be interrupted.

26. The molecular aggregate of claim 21, wherein Cm and Cm' represent a polymethylene chain having 0 to 12 carbon atoms.

27. The molecular aggregate of claim 21, wherein $\phi$ and $\phi'$ are selected from groups (1)-(4) below:

Group (1)

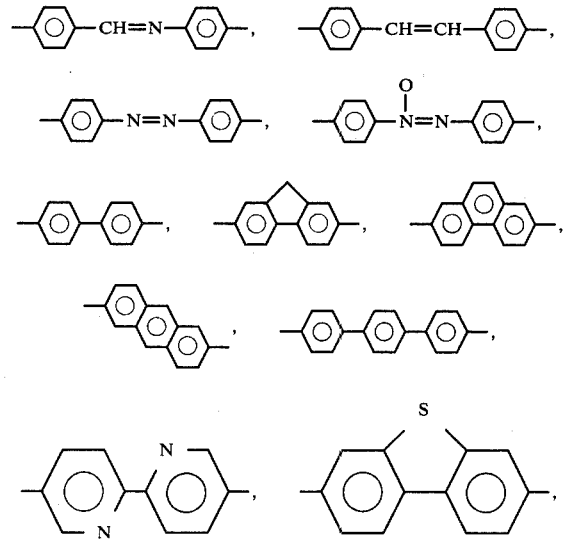

-continued
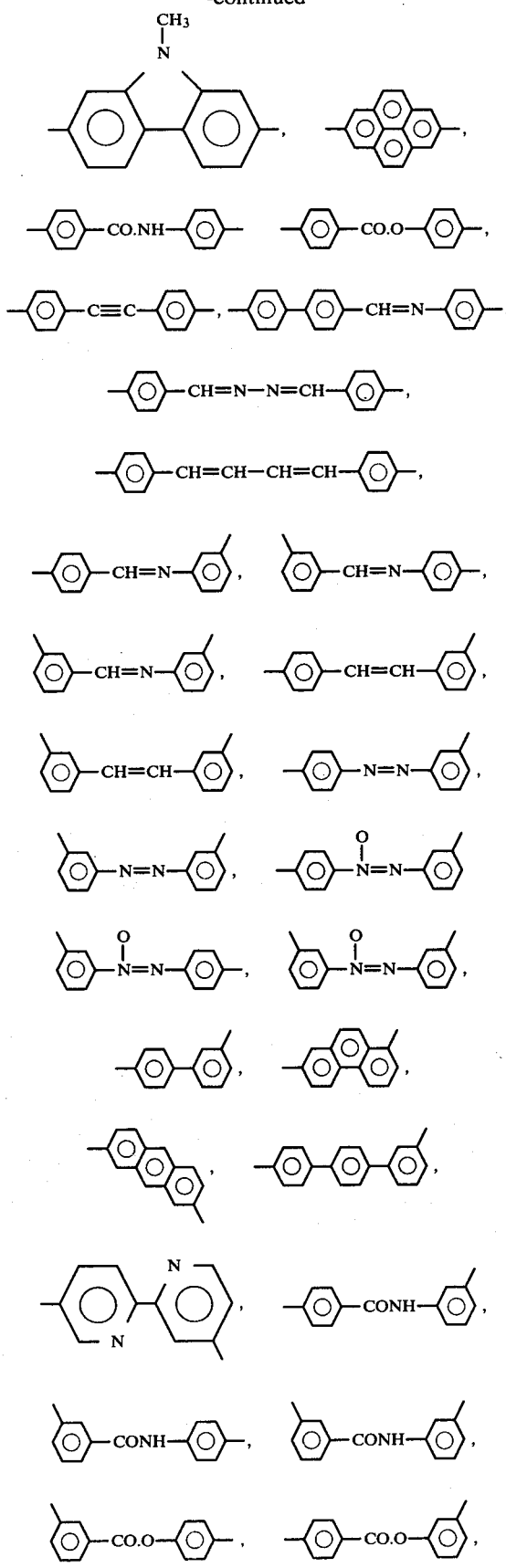
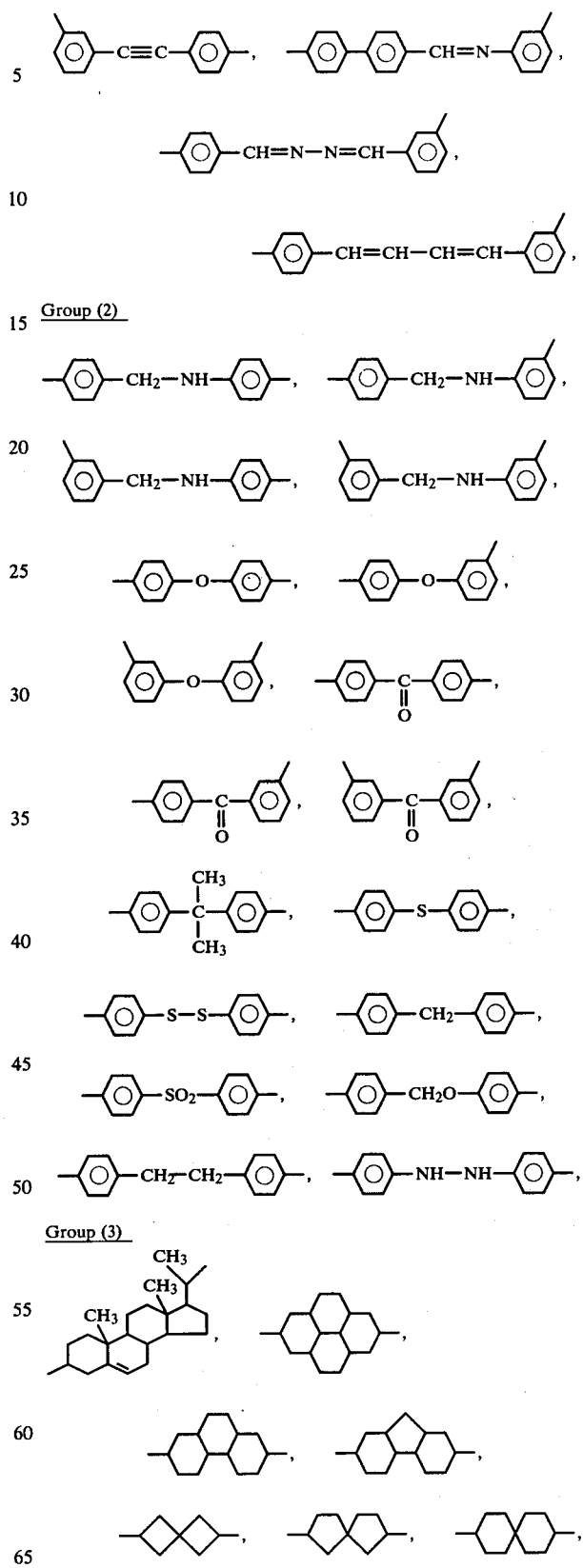
28. The molecular aggregate of claim 21, wherein said rigid moiety provides a generally linear or parallel relation between Ya—φ and Yb—φ or between Ya'—φ' and Yb', the axes thereof forming an angle of 20° or less.

29. The molecular aggregate of claim 21, wherein said X and X' represent a hydrophilic moiety selected from the group consisting of sulfonates and sulfonium salts.

30. The molecular aggregate of claim 21, wherein said X and X' represent a hydrophilic moiety selected from the group consisting of carboxylates.

31. The molecular aggregate of claim 21, wherein said X and X' represent a hydrophilic moiety selected from the group consisting of phosphates and phosphonium salts.

32. The molecular aggregate of claim 21, wherein said X and X' represent a hydrophilic moiety selected from the group consisting of polyols.

33. The molecular aggregate of claim 21, wherein said X and X' represent a hydrophilic moiety selected from the group consisting of ampholytic ions.

34. The molecular aggregate of claim 21, wherein said X and X' represent a hydrophilic moiety selected from the group consisting of ammonium salts, phosphates and polyethers.

35. The molecular aggregate of claim 21, wherein the surfactant is represented by formula (II).

* * * * *